(12) United States Patent
Oostman, Jr. et al.

(10) Patent No.: US 8,388,631 B2
(45) Date of Patent: Mar. 5, 2013

(54) SKIN TENSIONER FOR HAIR TRANSPLANTATION

(75) Inventors: Clifford A. Oostman, Jr., Hansville, WA (US); Steven E. Jakubowski, Mountain View, CA (US)

(73) Assignee: Restoration Robotics, Inc., San Jose, CA (US)

( * ) Notice: Subject to any disclaimer, the term of this patent is extended or adjusted under 35 U.S.C. 154(b) by 269 days.

(21) Appl. No.: 12/688,430

(22) Filed: Jan. 15, 2010

(65) Prior Publication Data

US 2010/0191253 A1 Jul. 29, 2010

Related U.S. Application Data

(60) Provisional application No. 61/146,872, filed on Jan. 23, 2009.

(51) Int. Cl.
*A61B 17/50* (2006.01)

(52) U.S. Cl. ............ 606/133; 606/187; 606/219

(58) Field of Classification Search ............ 606/133, 606/187, 1, 132, 131, 218, 217, 150, 204.35, 606/219; 600/431, 414, 426

See application file for complete search history.

(56) References Cited

U.S. PATENT DOCUMENTS

| | | | |
|---|---|---|---|
| 4,621,619 A | 11/1986 | Sharpe | |
| 4,896,680 A | 1/1990 | Hirshowitz | |
| 5,089,009 A | 2/1992 | Green | |
| 5,441,540 A | 8/1995 | Kim | |
| 5,449,374 A | 9/1995 | Dunn et al. | |
| 5,486,196 A | 1/1996 | Hirshowitz et al. | |
| 5,531,790 A | 7/1996 | Frechet et al. | |
| 5,662,714 A | 9/1997 | Charvin et al. | |
| 5,759,193 A | 6/1998 | Burbank et al. | |
| 5,769,783 A | 6/1998 | Fowler | |
| 5,785,649 A | 7/1998 | Fowler, Jr. | |
| 5,814,067 A | 9/1998 | Fleischmann | |
| 5,964,697 A | 10/1999 | Fowler, Jr. | |
| 5,971,920 A | 10/1999 | Nagel | |
| 5,972,021 A | 10/1999 | Huttner et al. | |

(Continued)

FOREIGN PATENT DOCUMENTS

| | | |
|---|---|---|
| DE | 44 44 130 A1 | 6/1995 |
| WO | 0103588 A1 | 1/2001 |

(Continued)

OTHER PUBLICATIONS

Non-Final Office Action mailed Dec. 20, 2011, in relation to commonly assigned U.S. Appl. No. 12/688,395 (11 pages).

(Continued)

*Primary Examiner* — Ryan Severson
*Assistant Examiner* — Tin Nguyen
(74) *Attorney, Agent, or Firm* — Lena I. Vinitskaya; Sharon Upham

(57) ABSTRACT

Devices and methods for applying tension to an area of skin are provided, for example, for follicular unit removal and implant in a hair transplantation procedure. The devices may include a frame with at least two skin contact members that hold to the skin. Also disclosed are various ways to apply a force displacing the skin contact members apart, thus creating tension in the skin. The devices and methods may incorporate suction, and/or barbs or microbarbs. The frame may surround the skin area with tensile forces applied outward in multiple directions or substantially uni-directionally. Adjusting members and indicators may be provided to control and display the tensile force applied to skin. The tensioning devices and methods may be incorporated into a robotic hair transplantation system.

42 Claims, 11 Drawing Sheets

U.S. PATENT DOCUMENTS

| | | | |
|---|---|---|---|
| 6,036,641 | A | 3/2000 | Taylor et al. |
| 6,120,436 | A | 9/2000 | Anderson et al. |
| 6,159,231 | A | 12/2000 | Looney et al. |
| 6,190,312 | B1 | 2/2001 | Fowler, Jr. |
| 6,254,624 | B1 | 7/2001 | Oddsen et al. |
| 6,695,868 | B2 | 2/2004 | Looney et al. |
| 7,208,006 | B2 | 4/2007 | Fleischmann |
| 2002/0087051 | A1 | 7/2002 | Levisman |
| 2003/0120298 | A1* | 6/2003 | Gildenberg ............ 606/187 |
| 2004/0049206 | A1* | 3/2004 | Rassman ............ 606/133 |
| 2007/0021779 | A1 | 1/2007 | Garvin et al. |
| 2007/0049970 | A1* | 3/2007 | Belef et al. ............ 606/232 |
| 2007/0078466 | A1 | 4/2007 | Bodduluri et al. |
| 2007/0282374 | A1* | 12/2007 | Sogard et al. ............ 606/219 |
| 2008/0027484 | A1 | 1/2008 | Lee et al. |
| 2008/0114395 | A1 | 5/2008 | Mathisen et al. |
| 2010/0030260 | A1 | 2/2010 | Fleischmann |
| 2011/0178533 | A1 | 7/2011 | Oostman et al. |

FOREIGN PATENT DOCUMENTS

| | | |
|---|---|---|
| WO | 2006132256 A1 | 12/2006 |
| WO | 2008/107110 | 9/2008 |

OTHER PUBLICATIONS

Invitation to pay Additional Fees Form PCT/ISA/206 and Annex to Form PCT/ISA/206 (communication relating to the results of the Partial International Search) in relation to PCT/US2010/021353, Applicant Restoration Robotics, Inc. dated Apr. 15, 2010. (7 pages).

PCT International Search Report in relation to commonly assigned PCT application, PCT/US2010/021353, Applicant: Restoration Robotics, Inc., Forms PCT/ISA/210, 220 and 237, dated Jun. 29, 2010 (20 pages).

Final Office Action mailed Aug. 16, 2012, in relation to commonly assigned U.S. Appl. No. 12/688,395 (16 pages).

Office Action dated Jun. 26, 2012, in relation to commonly assigned Australian Patent Application No. 2010206872 (3 pages).

Translation of Office Action dated Nov. 16, 2012, in relation to commonly assigned Korean Patent Application No. 10-2011-7017185 (5 pages).

* cited by examiner

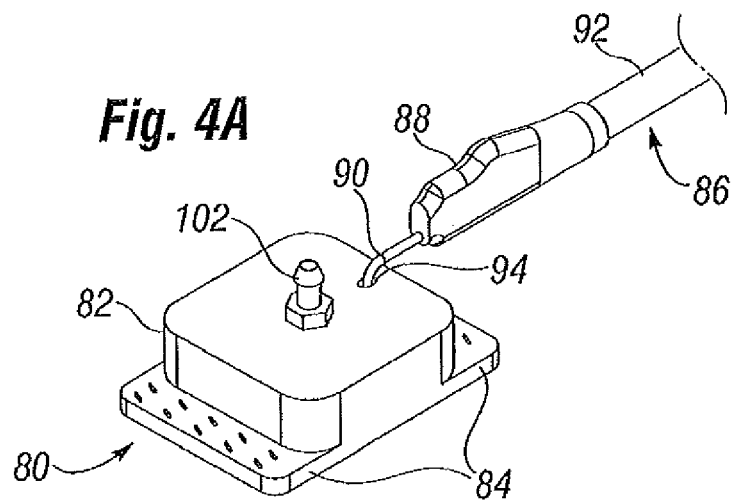
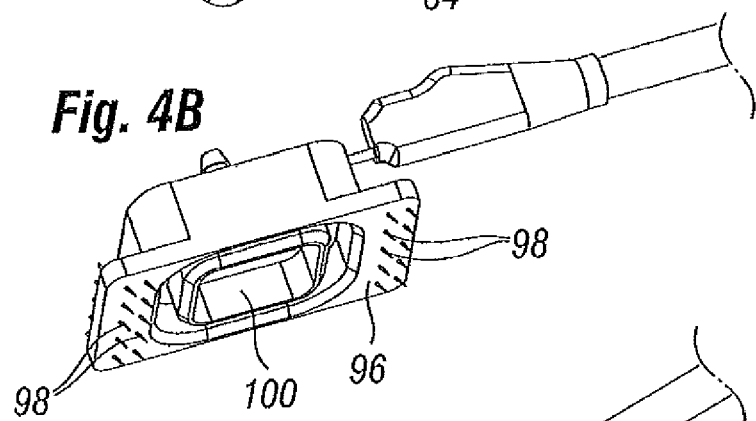
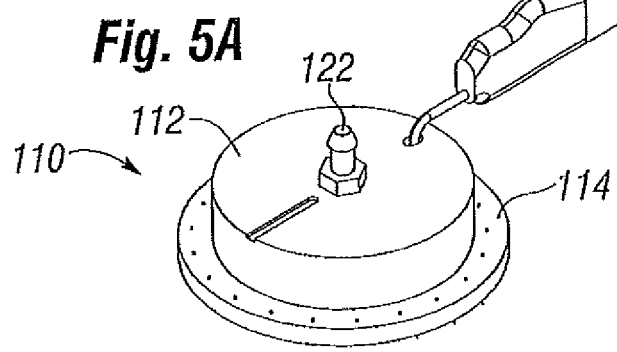
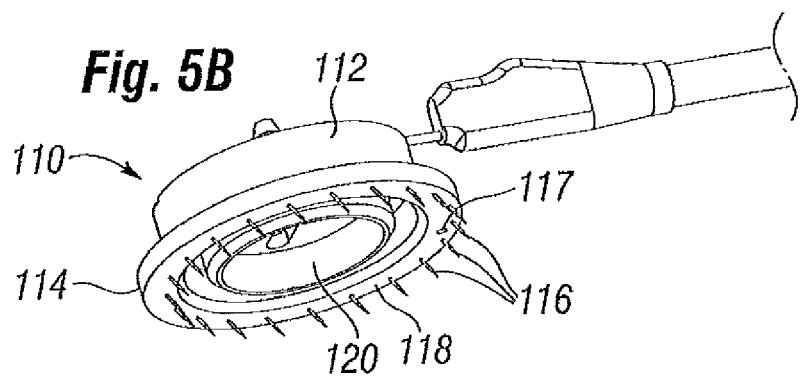

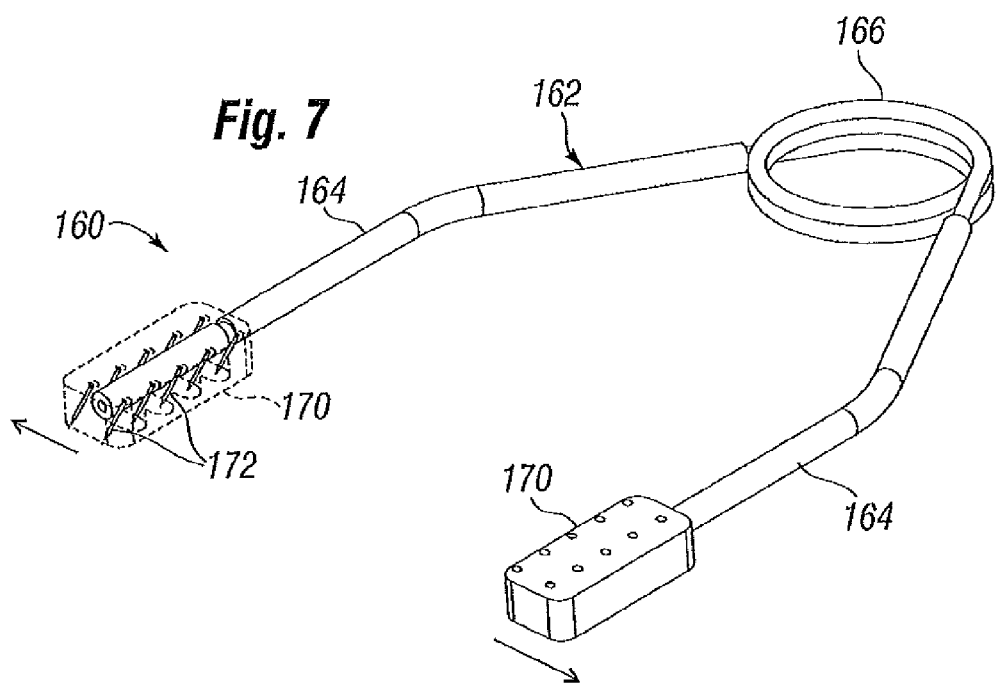
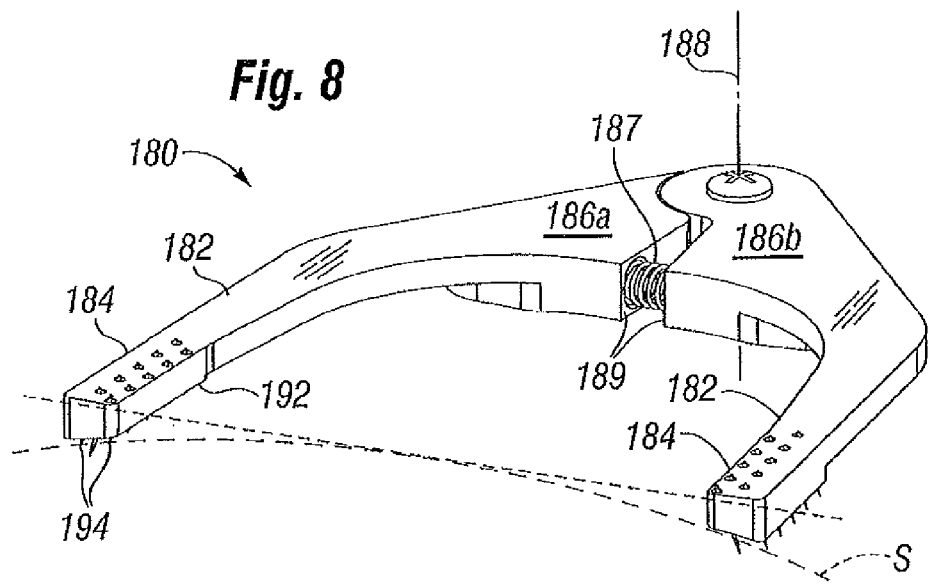

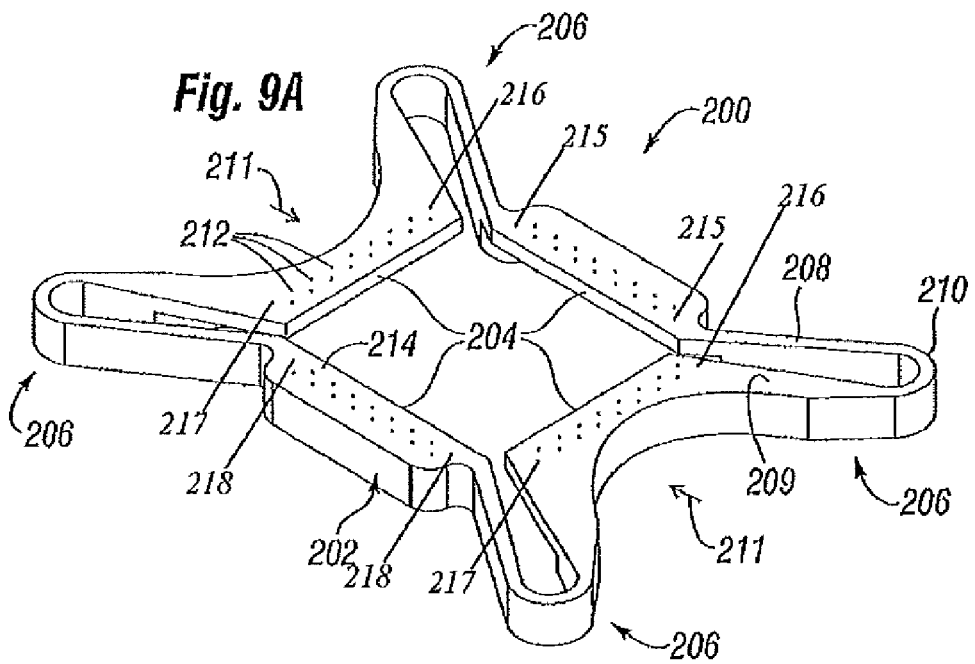
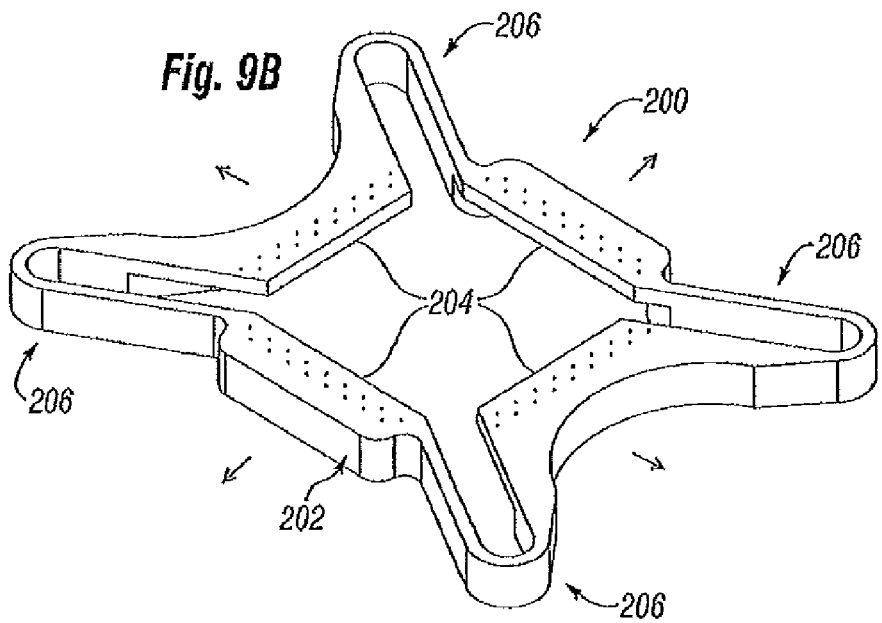

SKIN TENSIONER FOR HAIR TRANSPLANTATION

RELATED APPLICATIONS

This application claims priority under 35 U.S.C. 119(e) to U.S. Provisional Application No. 61/146,872 filed Jan. 23, 2009, entitled "SKIN TENSIONER FOR HAIR TRANSPLANTATION".

FIELD OF THE INVENTION

The present invention relates generally to devices, systems and methods for applying tension to an area of skin or a body surface and, in particular, skin tensioners and methods of use in conjunction with hair transplantation procedures.

BACKGROUND OF THE INVENTION

There are numerous surgical, cosmetic, therapeutic and dermatological procedures that involve maneuvering an area of skin. Hair transplantation is one of those procedures and it typically involves harvesting donor hair grafts from the "donor areas," and implanting them in a bald area ("recipient area"). There are various known tools and instruments used for harvesting and implantation of the follicular units ("FUs"), including various needles, punches, and forceps. Hair transplantation is very labor-intensive and complex procedure that requires skill and precision. During procedures manually performed by a physician, in order to tension a skin surface in the area of hair harvesting or implantation, pressure is typically applied adjacent the target location using two fingers. Similar skin tensioning technique is used in various cosmetic and dermatological procedures other than hair transplantation.

One automated system for harvesting follicular units from a body surface is disclosed in U.S. Patent Publication 2007/0078466. In one embodiment a skin tensioner in the form of two tines presses against a skin surface to thereby tension the skin and enable the FUs to stand more erect relative to the scalp surface.

There are commercially available surgical retractors that hold tissue away from the operating field, including those manufactured by Lone Star Medical Products, Inc. These retractors, however, are not very suitable for skin tensioning required for procedures, such as hair transplantation.

SUMMARY

The present application discloses various skin or body surface tensioning devices and methods that may be applied to a scalp, skin or other body surface area during various medical, cosmetic, or dermatological procedures. Such devices are especially useful, for example, when harvesting and/or implanting hair follicles or follicular units (FUs). In certain embodiments, the skin tensioning devices enable monitoring of the magnitude of the tension applied to the skin, and adjustment thereto if necessary. Furthermore, the tensioning devices disclosed are relatively easy to apply by one person or one hand, and may be easy to remove and reapply. Thus, the devices may be easily removed from the treatment area to allow the patient to get up and move around in the middle of the procedure if desired. Another advantage of various embodiments described herein is that the skin may be placed under substantially uniform or even tension across a treatment area. The devices may be relatively inexpensive to manufacture and certain parts may be disposable to facilitate cleanup and remit reuse of easy to sterilize components. Further, the device may be provided with the ability to suction away blood and flush with saline. In addition the device may be provided with suction to more securely hold the skin tensioning device against the body surface. In combination with an imaging system, the tensioning device may provide a platform for fiducials.

According to one aspect, a device for applying tension to a body surface comprises a flexible frame, the flexible frame comprises a skin contact member having at least one skin grasper. The flexible frame is configured to move between a compressed configuration and a relaxed configuration due to inherent flexibility of the frame. The flexible frame is also biased in the relaxed configuration, and in the relaxed configuration, when the at least one skin grasper is engaged in the body surface, the flexible frame is configured to provide tension in the body surface. The frame may inherently be flexible due to the selected material of choice, for example, a resilient material, elastic in nature; and/or may be flexible due to shape, structure, gaps, thickness, or other such design choices incorporated into parts of or into the entire frame that render the frame flexible. The body surface tension device may apply a substantially uniform tension across the body surface, or it may apply tension in one or more directions across the body surface, depending on the embodiment and desired features. In another embodiments, the frame may comprise a plurality (for example, at least three) side sections, and compression of two of the at least three side sections causes at least three of the side sections to converge. Various skin graspers may include, for example, a barb(s), a microbarb(s), an adhesive, a rough surface texture, or any other similar structures or features.

According to a further aspect, a compression tool for use with the tensioning devices of the present application is provided. The compression tool is shaped and configured to engage the frame of the tensioning device and to cause the frame to move between the compressed and the relaxed configuration. The general plane of the compression tool (when positioned to engage the frame and to move it between the compressed and the relaxed configurations) can be substantially parallel to the general plane of the frame of the tensioning device, or it could be a different general plane, for example, substantially orthogonal to the plane of the frame.

According to yet further aspect of the disclosure, a device for applying tension to a body surface includes a frame comprising a skin contact member having a plurality of skin graspers, the frame configured to be operable to move between a compressed configuration and a relaxed configuration; and wherein, when positioned on the body surface in the compressed configuration, at least one of the plurality of the skin graspers is directed at a first angle with respect to the body surface, and in the relaxed configuration the at least one of the plurality of the skin graspers is directed at a second different angle with respect to the body surface. In some embodiments, the first angle may be substantially orthogonal to the body surface and the second angle may be an angle other than substantially orthogonal to the body surface. Also, the frame may be a flexible frame, operable to flexibly move between the compressed and relaxed configurations. The above device may be used with a compression tool, for example as described above, wherein the compression tool is shaped to engage the flexible frame and is configured to cause the at least one of the plurality of the skin graspers to move between the first and the second angle. Similar to the other described embodiments, frame of the above device may lie generally in a first plane (including a curved plane), and the compression tool may be configured to be positioned generally in a second plane when causing the frame to move between the compressed and the relaxed configurations. The second plane may be, for example, substantially parallel to the general plane of the frame, or substantially orthogonal to the general plane of the flexible frame.

According to still further aspect, a device for applying tension to a body surface is disclosed. The device comprises a frame configured to move between a compressed configuration and a relaxed configuration, the frame comprising at least three contact members, each contact member having at least one skin grasper. The frame is further configured such that compression of two of the at least three contact members causes the at least three of the contact members to converge to the compressed configuration. Therefore, the frame could be conveniently compressed just with one hand, either manually or using a compression tool and wherein the frame is configured to facilitate tensioning of the body surface in the relaxed configuration when the at least one skin grasper is engaged in the body surface. The frame may be configured to conform to the body surface. In some embodiments, a first of the at least three contact member may lie in a first plane, and a second of the at least three contact members may lie in a plane other than the first plane.

Features of the skin tensioner described in reference to one embodiment may be combined with one or more features described in reference to one or more of the other embodiments. Also, any of the described tensioning devices may include at least one channel in the frame in fluid communication with one or more openings on a skin contact member of the frame for placing the openings in fluid communication with a source of reduced pressure so as to apply suction to the skin. Alternatively, the tensioning devices may include an indicator, for example, on the frame that displays the magnitude of the tensioning force; or a tension control on the frame that enables adjustment of the magnitude of the tensioning force.

Also, methods for applying tension to a body surface, for example, in use during hair harvesting and/or implantation are disclosed. According to one aspect, the method comprises using an inherent flexibility of a flexible frame to move the flexible frame from a relaxed configuration to a compressed configuration. The flexible frame may comprise a skin contact member having at least one skin grasper; and the method further comprises placing the skin contact member of the flexible frame on the body surface such that the at least one skin grasper engages the body surface and releasing the flexible frame to cause the frame to move from the compressed configuration to the relaxed configuration such that tension is created across a treatment area in the body surface. According to another aspect, a method of applying tension to a body surface may comprise compressing a frame of a tensioning device in N directions to cause the frame to compress in more than N directions. According yet to another aspect, a method of applying tension to a body surface may comprise moving a frame of a tensioning device from a compressed configuration to a relaxed configuration such that to cause at least one skin grasper positioned on the frame to move from a first angle relative to the body surface to a second angle relative to the body surface. Any of the methods described herein may further comprise using a compression tool to engage the flexible frame, and to cause the flexible frame to move between the compressed and the relaxed configurations. Similarly, any of the methods may comprise harvesting hair grafts from the body surface or implanting hair grafts into the body surface in the treatment area. As will be understood from the detailed description, one or more steps of the various methods of applying tension to a body surface described herein in reference to different embodiments may be combined together or otherwise performed in the same method

BRIEF DESCRIPTION OF THE DRAWINGS

Features and advantages of the inventions described herein will become appreciated as the same become better understood with reference to the specification, claims, and appended drawings wherein:

FIGS. 4A and 4B are perspective views of a skin contact member which can be used with the skin tensioner that incorporates suction and barbs;

FIGS. 5A and 5B are perspective views of an alternative skin contact member which incorporates suction and skin graspers, such as barbs;

FIG. 7 is a perspective view of a skin tensioner having a coil-spring frame with bifurcated legs each having a skin contact member thereon that incorporates barbs;

FIG. 8 is a perspective view of a skin tensioner having a compass-like frame with bifurcated legs each having a skin contact member thereon that incorporates barbs;

FIGS. 9A and 9B are perspective views of a butterfly-style skin tensioner frame shown, respectively, in inwardly compressed and relaxed views;

DETAILED DESCRIPTION OF THE PREFERRED EMBODIMENTS

Figure 1:
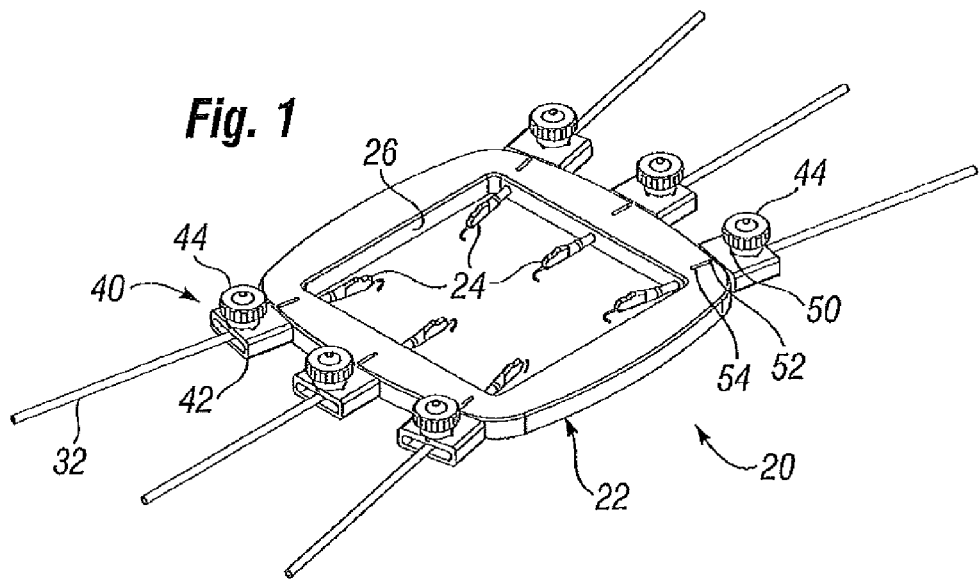
FIG. 1 is a perspective view of a first embodiment of a skin tensioner having a closed-loop frame, a plurality of independently adjustable skin contact members and a tension control mechanism.

In the following Detailed Description reference is made to the accompanying drawings that show by way of illustration specific embodiments in which the invention may be practiced. In this regard, directional terms, such as "top," "bottom," "front," "back," "side", "distal," "proximal," etc., are used with reference to the orientation of the Figure(s) being described. Because components or embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following Detailed Description, therefore, is not to be taken in a limiting sense, and the scope of the present invention is defined by the appended claims.

It has been found that commercially available surgical retractors, such as that manufactured by Lone Star Medical Products, Inc. do not provide uniform and consistent skin stretching across the treatment area. Moreover, they are difficult to install, remove, and reinstall if a patient needs to rest. The present application describes a number of systems and methods of use for creating tension across a skin or body surface to facilitate various procedures on the body surface, for example, harvesting of follicular units (FUs). For purposes of clarity, creating tension in a skin surface means applying a tensile force such that the skin surface exhibits lateral tension greater than any tension existing in the relaxed state. Typically, this requires pulling apart, or applying separating forces to, at least two spaced locations, with the area in between experiencing tension. It should be understood that the tension can be uni-directional, along a single axis, or multi- and even omni-directional. For example, a circular frame that pulls the skin surface apart evenly in all directions sets up an omni-directional tension in the inner circular region.

To apply tensile forces to the skin surface, the systems described herein incorporates at least two or more spaced-apart skin contact members. The skin contact members each define a skin contacting surface that will lie against the skin surface. The skin contacting surface features some means of holding the skin contact member to the skin surface, such as suction in certain embodiments. In order to hold the skin contact member to the skin surface, however, the system need only increase the lateral resistance to movement of the skin contact member across the skin surface from the resistance required to move a smooth-bottomed member across the skin surface absent any external downward pressing force.

One way to increase the lateral resistance to movement of the skin contact members is to provide barbs on the skin contacting surface. In the context of the present application, a "barb" means any small element that projects from the skin contact member below the skin contacting surface to puncture or form a depression in the skin surface. That is, a barb does not necessarily have to be sharp so as to be capable of puncturing the skin surface. The term "barb" therefore incorporates needles, pins, points, hooks, nubs, projections, and other similar terms. Furthermore, in certain embodiments and applications of the invention, it is beneficial to use the term "microbarbs." The term "microbarb" refers to a small barb having a maximum size characteristic, typically its diameter (or cross-sectional dimension regardless of the shape; reference in this context to the diameter does not mean that the cross-section is necessarily circular). For example, in one embodiment the microbarb comprises a barb that has a diameter of about 0.127-0.305 mm (0.005-0.012 inches). Also, the microbarb may be defined relative to the barb in terms of surface density, for example, the size of the microbarbs allows them to be placed within 1-5 mm from each other and to more uniformly cover the surface area. Larger barbs, on the other hand, require greater spacing and thus present a less dense array.

Although barbs are described herein as a primary means of ensuring good grip of the skin contact members to the skin, other solutions that merely increase the coefficient of friction are contemplated. For instance, skin contact members having adhesive may be successfully utilized in conjunction with certain aspects described herein. Another possibility is mating Velcro patches, with one temporarily adhered to the skin and one on the skin contact member. As such, the term "skin grasper" as used herein encompasses various means of holding the skin contact member to the skin surface by increasing the lateral resistance to movement of the skin contact member across the skin surface in contrast to a smooth-bottomed surface. That is, "skin graspers" encompass barbs, microbarbs, suction, adhesives, Velcro, ribs, ridges, pins, etc., and even rough surface texture. Although the presence of one or more of such structures on an item secured to skin may be known in the abstract (e.g., an adhesive bandage), it is believed that their usage in conjunction with inducing tension across a treatment area is novel, in particular in the context of hair transplantation. Moreover, various other features of the skin tensioners described herein in combination with one or more of these skin graspers are believed novel.

The adjective "automated" with reference to a system or process as a whole means that some part or all of a particular system or step in the process involves an autonomous mechanism or function; i.e., that mechanism or function does not require manual actuation. Ultimately, one or more steps in the procedure may be automated, or autonomous, with some parts requiring manual input. This definition encompasses an automated system that requires only an operator to depress an ON switch or schedule the operation, and also a system in which hand held tools are used but some mechanism of the system functions autonomously, i.e., without human input, to perform a function. Some automated processes may also be robotically-assisted or compute/software/machine-instruction controlled. The devices and methods of the present invention are useful in manual procedures and systems, as well as in automated procedures and system, and they are especially useful in the robotically-assisted systems and procedures. In contrast, the adverb "automatically" when referred to use of a particular component of a system or a particular step in a process means that such step is accomplished autonomously, i.e., without real-time manual assistance. The terms "coupled," or "attached," or "connected," or "mounted" as used herein, means directly or indirectly coupled, attached, integrated, or mounted, for example, through one or more intervening components.

According to one aspect of the present application, a skin tensioner is provided that allows control of the tension and provides substantially uniform tension across the relevant treatment area. In a first embodiment of the present application, FIG. 1 illustrates a skin tensioner 20 having a closed-loop frame 22 and a plurality of independently adjustable skin contact members 24. In this embodiment, the frame 22 features a substantially square inwardly-facing wall 26 defining the periphery of a similarly-shaped aperture into which the skin contact members 24 project. A plurality of the skin contact members 24 are shown to project from each of two opposite parallel sides of the wall 26, although they may be provided in all four sides. Moreover, as will be apparent from the description of alternative embodiments, the frame 22 need not be a closed loop, nor need it define a rectilinear aperture, or have an even number of sides. For example, the aperture may be circular or oval, or triangular.

The frame 22 provides structure to which the movable skin contact members 24 mount and which provides rigid support thereto. FIG. 1 illustrates three skin contact members 24 projecting inward from each of the two opposed parallel sides of the frame inner wall 26. As will be explained below, the frame 22 is designed to be placed on a skin surface with the skin contact members 24 applying tension or stretching the skin within the frame aperture. That is, each skin contact member 24 extends inward from the frame 22, contacts the skin surface and is secured thereto in some manner, and exerts an outward force parallel to the skin surface toward the outer frame.

Figure 2:
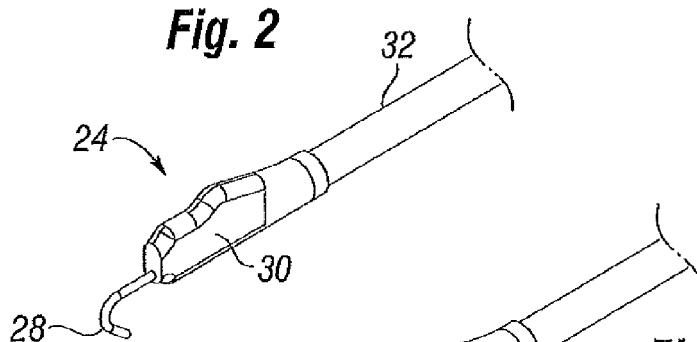
FIG. 2 is an enlarged perspective view of one example of a skin contact member shown in FIG. 1.

In one particular embodiment, each of the skin contact members 24, as seen enlarged in FIG. 2, may include a barb or hook 28 on the distal end of a finger 30. Each finger 30, in turn, connects to an elongated, flexible strand 32 (or alternatively, a metal wire 32) that passes outward through an opening in the inner wall 26 of the frame. The barb or hook 28 may be inserted through an incision formed in the skin surface so that the skin contact member 24 can apply tension when subject to an outward force. Alternatively, the hook 28 may have a sharp tip suitable for puncturing the skin surface so that a previously-formed incision is unnecessary. Still further, instead of directly engaging the skin surface, the hook 28 may engage a different skin contact member, and therefore may merely function as a link in an overall tension mechanism.

The skin tensioner 20 incorporates a mechanism for controlling an outward force on each of the skin contact members 24. In the illustrated embodiment, each flexible strand 32 extends outward through an opening in the frame 22. There are numerous ways to apply an outward force to the flexible strands 32 and in turn the skin contact members 24. For example, each flexible strand 32 may be elastic and fixed to the frame 22 such that it may be stretched before engaging the corresponding barb or hook 28 with the skin surface. In the illustrated example, each flexible strand 32 passes through a tension adjuster 40 either mounted in the frame 22 or provided as a separate element as shown on the exterior of the frame. In a simple embodiment, each tension adjuster 40 includes a housing 42 having a through bore for receiving a strand 32, and a knob 44 connected to a shaft (not shown) intersecting the through bore that applies a frictional force to the strand therein. For example, the knob 44 may connect to a threaded shaft received in a similarly threaded bore in the housing 42 so that the shaft can be tightened on the strand 32 in the manner of a set screw. A free end of the strand 32 may be manually pulled outward until a desired tension is established in the skin surface, at which point the user actuates the knob 44 to secure the position of the strand relative to the housing 42 and frame 22. In this regard, the strand 32 may be elastic as mentioned above, or relatively inelastic, such as a stainless steel wire. In either case, engaging the skin contact member 24 with the skin surface and pulling outward creates tension in the skin surface.

In an alternative embodiment, each or any of the tension adjuster 40 incorporates an inner spool or friction wheel (not shown) for pulling on the associated flexible strand 32. For example, the flexible strand 32 may wrap around a spool rotated by the knob 44. This provides the user with greater control of the amount of tension in the flexible strand.

According to another aspect of the application, the skin tensioner 20 may indicate the amount of tension, for example, in each of the flexible strands 32. For example, in the just-described embodiment of the tension adjuster 40 having a spool, the knob 44 may have markings such that the number of rotations may be monitored with the level of tension being relative to the extent of rotation. In an illustrated embodiment, the shaft depending from each knob 44 engages the associated flexible strand 32 through a linear slot 50 in the housing 42. A pin 52 connected to either the flexible strand 32 or knob 44 translates within another linear slot 54 in the frame 22. The pin 52 is spring-biased outward within the slot 54, and translates inward along the slot 54 when the tension in the flexible strand 32 exceeds the spring bias. Therefore, as the pin 52 moves inward it provides a visual indicator of the amount of tension in the flexible strand 32. Calibrated markings may also be provided next to and along the slot 54.

Of course, there are numerous other ways to indicate tension in the flexible strands 32, such as more complicated and typically more expensive analog or digital numerical force displays. The present application contemplates any number of indicators from the most simple to the most involved. Furthermore, either or both of the tension control mechanism and tension indicators may be incorporated into any of the skin tensioners described herein, and the lack of an illustrated tension indicator or tension control should not be construed as excluding one. Tension indicators help the user establish the proper skin tension. A minimum level of tension is desired, in particular for hair follicle removal to smooth the skin surface and encourage the follicular units to stand up straight. Furthermore, a predetermined minimum level of tension helps a removal tool such as a needle pierce the skin without cutting excessive flaps of skin around the follicular unit. However, the tension should be limited to a maximum to avoid excessive trauma to the skin surface. Finally, indicators of tension in each flexible strand enable the user to balance the amount of tension to avoid applying too much to one location or another.

Figure 3A:
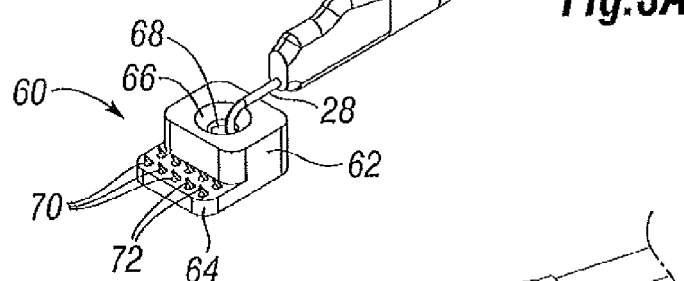
FIGS. 3A and 3B are perspective and side elevational views of an alternative skin contact member which can be used with the skin tensioner.
Figure 3B:
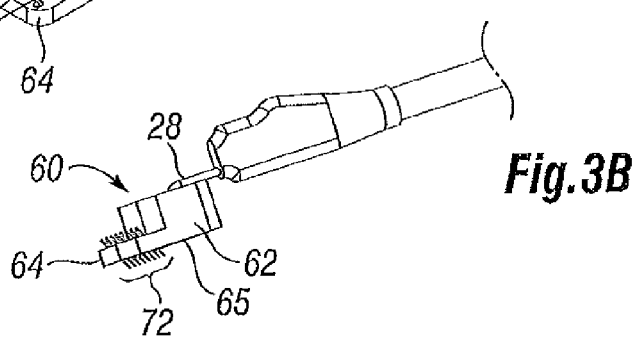

FIGS. 3A and 3B are perspective and side elevational views of an alternative skin contact member 60 which can be used with the skin tensioner described herein. As mentioned above, it may be beneficial to eliminate or reduce the wound that could be created by use of the certain barbs, such as the hook 28 shown in FIG. 2. Moreover, in certain applications using a small number (e.g. 6-10) of the relatively large hooks 28 may not provide a sufficiently uniform stretching of the skin over a whole treatment area. For example, the skin tension in the areas around the location of the hooks may be sufficient but in the spaces between the hooks, the skin may not be tensioned or stretched enough for such procedures like hair harvesting and implantation. Or, the tension established by relatively few spaced-apart hooks may be uneven, resulting in sub-optimal tension in some areas. Therefore, hooks 28 of FIG. 2 may be completely avoided or used solely as an intermediate link to alternative skin contact members, such as those shown at 60 in FIG. 3A. Although other ways to couple or connect the flexible strand 32 to the skin contact member 60 are contemplated without the use of hooks 28, the hooks 28 on the aforementioned skin contact members 24 may be used as they enable the entire frame 22 to be quickly removed. Furthermore, the hooks 28 (or similar expedient) are generic and couple to any number of different skin contact members.

An example of a skin contact member 60 includes a coupling body 62 having a generally horizontal flange 64 extending therefrom defining on its bottom a skin contacting surface 65. The coupling body 62 includes an upper tapered aperture 66 leading to a hole 68 that can be engaged by the hook 28 or other alternative connector 28. The tapered shape of the aperture 66 helps in quickly inserting the connector 28. The flange 64 includes a plurality of perforations or bores 70 through which pass a plurality of microhooks or microbarbs 72 (as described below) having sharpened ends that project below the skin contacting surface 65 and create more uniform stretching by distributing the force across a larger area of skin. As an additional benefit, the microbarbs 72 are desirably sized so as to eliminate or reduce the creation of the wound that requires healing. In the illustrated embodiment, the bores 70 are angled downward in a proximal direction to enhance the ability of the microbarbs 72 to anchor in the skin surface, however the angle of the bores is not limited to that illustrated. The microbarbs 72 may be straight pins or needles that are easily inserted and fixed within the bores 70, such as with a suitable adhesive. Alternatively, the microbarbs 72 may be curved or angled, and may be fixed in the material of the flange 64 during a molding process. The reader will understand there are numerous ways to provide downwardly projecting microbarbs on the skin contact member.

There is at least one barb 72 provided on the skin contact member 60, but preferably a plurality are included to enhance the gripping effect to the skin surface. Moreover, increasing the number of barbs 72 is desirably coupled with a reduction in their size. In a preferred embodiment, there are at least four and preferably ten or more barbs 72 which will be termed herein "microbarbs" as previously explained. Furthermore, the length of the microbarbs 72 that extends below the skin contacting surface 65 is desirably less than about 5 mm, and preferably, between 1 and 4 mm.

As mentioned above, the "barb" and "microbarb" are examples of various "skin graspers" or "skin grabbers" which should be construed to cover any number of downward projections from the skin contacting surface 65. Such downward projections could be, for example, molded points, pins or ribs on the underside of the skin contact member 60. The use of sharpened elements such as the barbs 72 that pierce the skin surface is but one alternative.

In use, with reference to the example illustrated in FIG. 1, the user positions two or more of the skin contact members 60 on a skin surface in spaced relationship and applies a tensile force tending to separate the members. For example, six skin contact members 60 may be used in conjunction with the skin tensioner 20 illustrated in FIG. 1, with the six hooks 28 attaching to the respective coupling bodies 62. Pulling on the flexible strands 32 from the frame 22 places in tension the skin surface between the two rows of three skin contact members 60.

According to another aspect of the application, FIGS. 4A and 4B are perspective views of a skin contact member 80 that can be used, for example, with the skin tensioner 20 of FIG. 1 or other variants, and incorporates suction as well as barbs. The skin contact member 80 includes a central coupling body 82 and a pair of oppositely-directed flanges 84. A tension-applying member 86 couples to an upper surface of the coupling body 82. The member 86 may be, for example, identical to the skin contact member 24 described above with respect to FIGS. 1 and 2, and thus may include a finger 88 having a distal hook 90 and a flexible strand 92 extending a proximal direction. The hook 90 may engage a small aperture 94 in the top surface of the coupling body 82, or other similar feature. Alternatively, the member 86 may have a connector 90 (instead of the hook), or it may be otherwise mounted or connected to the skin contact member 80.

The flanges 84 each have skin contacting surfaces 96 on their undersides from which a plurality of microbarbs 98 project. In the illustrated embodiment there are ten such microbarbs 98 on each flange 84 all angled downwardly in a proximal direction. The flanges 84 and microbarbs 98 may be similar to those described above with respect to FIGS. 3A and 3B. The barbs and microbarbs may be arranged in multiple rows, or they may be staggered to achieve higher density. Also, some of the barbs may have different depth compared to the other barbs, for example, the depth of barbs may range approximately between 1 and 4 mm. For example, one row of barbs may have the same depth of 1 mm while the other row of barbs may have a depth of 2 or more mm.

In addition to the microbarbs 98, suction enhances resistance to lateral movement of the skin contact member 80 across a skin surface. More particularly, as seen in FIG. 4B the underside of the coupling body 82 includes a hollow foot 100 defining a central cavity. A nipple 102 projecting upward from the top of the coupling body 82 provides access to the central cavity. A tube or conduit transmits reduced pressure or suction via the nipple 102 into the central cavity. Because the hollow foot 100 extends approximately as far as to be level with the skin contacting surfaces 96 of the flanges 84, it also contacts the skin surface to form a seal and create a vacuum within the central cavity. The hollow foot 100 may be formed of an elastomeric material so as to enhance the seal.

FIGS. 5A and 5B show another skin contact member 110 that is much like the member 80 described above. Where the member 80 was generally rectilinear having proximally and distally directed flanges 84, the skin contact member 110 is substantially circular in plan view, and has a cylindrical coupling body 112 surrounded by a circular outer flange 114. A circular array of barbs or microbarbs 116 extends downward from a skin contacting surface 118 on the underside of the flange 114. A hollow tubular foot 120 project and downward in a space within the coupling body 112 to the level of the skin contacting surface 118. Again, a suction tube may be connected to an upper nipple 122 to create a vacuum within the tubular foot 120 against a skin surface.

In one variation, the tubular foot 120 may be divided in a plurality of pockets, each pocket having its own vacuum attachment and being connected to its own suction port or nipple 122 (or, there may be one suction port and a selector of some sort to open fluid communication with different pockets). This way, instead of creating vacuum within the whole surface area of the tubular foot 120 (and potentially causing blood rushing resulting in a "bruise-like" black and purple mark in case of a prolonged procedure), multiple areas of vacuum could be created and repeatedly and/or sequentially turned on and off to avoid prolonged pressure on a particular skin surface portion within the same pocket.

Sometimes, the tension applying member 86 (FIG. 4A) pulls on the skin contact member 110 in a way that it may cause its rotation or angling relative to the skin surface. To mitigate this effect, a small hole or opening 117, as shown in FIG. 5B, may be provided near the barbs 116. An elastic tube or similar pulling connector may be attached through the hole 117 and connected to the tension-applying member 86 to apply the force lower on the skin contact member 110 without creating a moment or rotation.

Figure 6A:
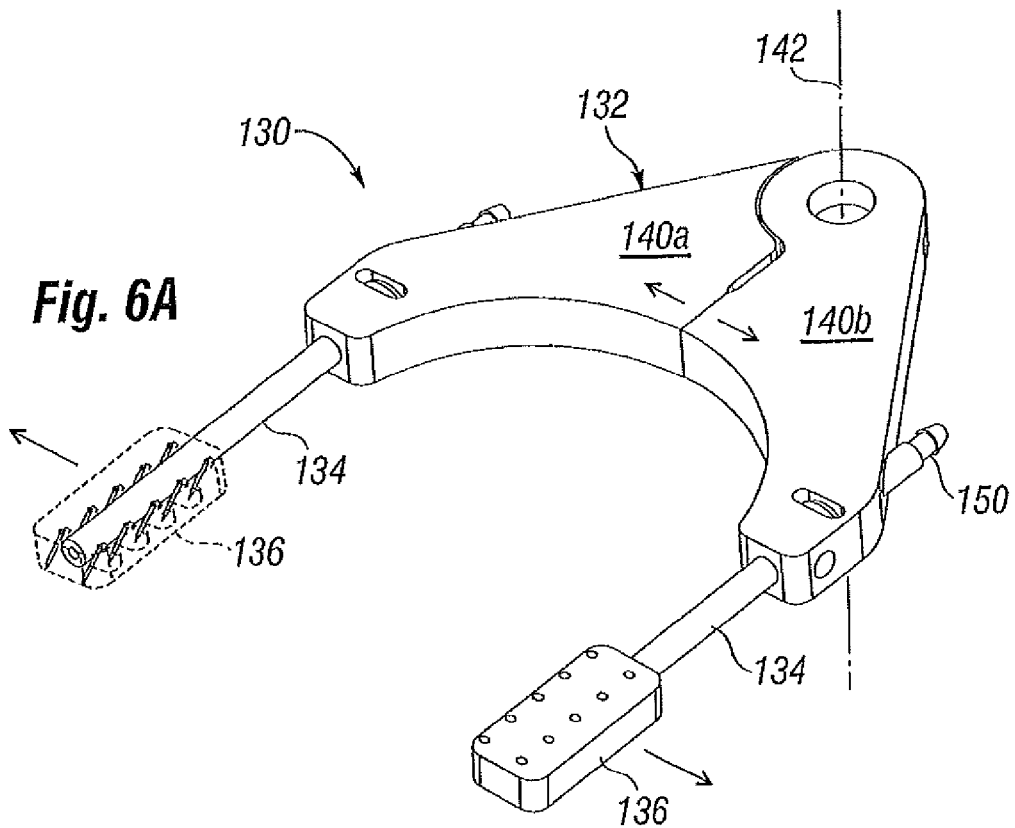
FIG. 6A is a perspective view of an alternative skin tensioner having a compass-like frame with bifurcated legs each having a skin contact member thereon that incorporates suction and barbs.

FIG. 6A is a different skin tensioner 130 than described above that has a compass-like frame 132 with bifurcated legs 134 each having a skin contact member 136 thereon incorporating both suction and barbs. The frame 132 includes a pair of base members 140a, 140b pivotally connected about a vertical axis 142. Although not shown, the frame 132 preferably incorporates a spring or other such biasing member, for example, as shown in FIG. 8, in between the base members 140a, 140b tending to spread them apart.

Figure 6B:
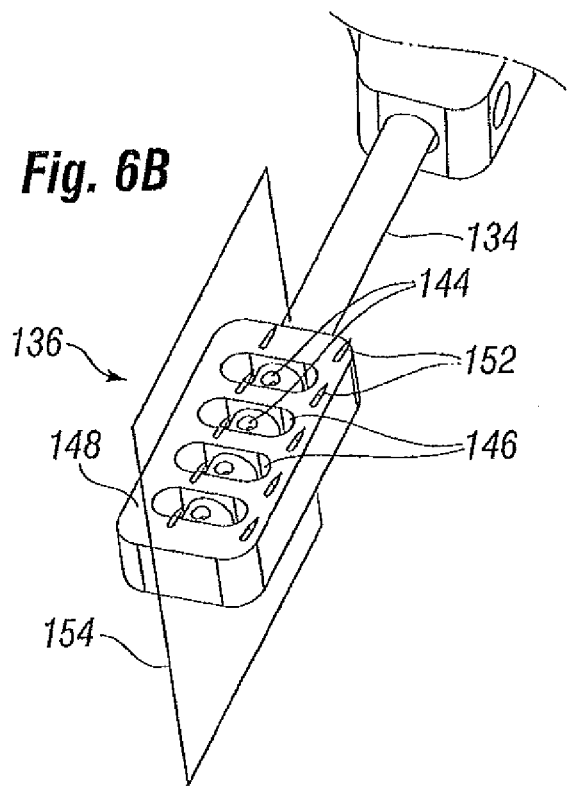
FIG. 6B is an enlarged perspective view of the underside of one of the skin contact members from FIG. 6A.

FIG. 6B is an enlarged perspective view of the underside of one of the skin contact members 136 from FIG. 6A. Each of the legs 134 is a hollow tubular member that has a plurality of ports 144 opening to a central lumen. Each one of the ports 144 opens at a plenum chamber 146 defined within the associated skin contact member 136. The plenum chambers 146 open downwardly in a skin contacting surface 148. The proximal end of each of the tubular legs 134 terminates in a nipple 150 to which a suction tube can be attached. By placing the skin contacting surface 148 on a skin surface, and providing suction to the lumen of the tubular leg 134, a vacuum can be created within each of the plenum chambers 146 holding the skin contacting member 136 against the skin surface.

As mentioned, the bifurcated frame 132 includes a spring or other mechanism for spreading apart the base members 140a, 140b, and in turn spreading apart the skin contact members 136. To enhance the ability of the skin contact members 136 to hold to the skin surface, an array of barbs 152 is provided in each. In the illustrated embodiment, there are ten barbs 152 projecting below the respective skin contacting surfaces 148 of each skin contact member 136, although this number may be as small as one and more than ten. The barbs 152 desirably angled downwardly and away from the opposite skin contact member 136. More particularly, as seen in FIG. 6B each of the barbs 152 is angled relative to a vertical midplane 154. Angling the barbs 152 in one skin contact number 136 away from the other enhances their ability to anchor to the skin surface and create tension therein.

FIG. 7 shows a skin tensioner 160 much like the device of FIG. 6A in that it incorporates a frame 162 with bifurcated legs 164. A central portion of the frame 162 comprises a coil spring 166 that acts as a pivot and provides a return spring force to the legs 164 if displaced from a relaxed configuration. In one embodiment, the relaxed configuration is shown with the distal portion of the legs 164 extending in parallel, although other arrangements are possible.

Each of the bifurcated legs 164 terminates at a distal end in a skin contact member 170 that incorporates barbs 172 projecting below a lower skin contacting surface. As with the earlier embodiment, the barbs 172 in one or more of the skin contact members 170 may be angled downwardly and away from the other skin contact member. The skin tensioner 160 shown in FIG. 7 includes no suction, although those of skill in the art will understand that suction can be provided much like the earlier-described embodiment. In use, the user squeezes the bifurcated legs 164 toward one another before pressing the skin contact members 170 onto a skin surface. The resultant outward spring bias created by the coil spring 166 tends to spread the skin contact members 170 apart (as shown by the arrows) and apply tension to the skin surface therebetween.

FIG. 8 illustrates another skin tensioner 180 again with a compass-like frame with bifurcated legs 182 each having a skin contact member 184 thereon. As with the embodiment of FIG. 6A, the frame includes a pair of base members 186a, 186b arranged to pivot about a vertical axis 188 and biased apart by a spring 187 positioned in a space therebetween. Two side walls 189 of the gap provide a hard stop to set a minimum spacing between the legs 182 and skin contact members 184 thereon. A user squeezes the base members 186a, 186b together until the side walls 189 touch, applies the spaced apart skin contact members 184 to the treatment area, and releases the frame. The spring 187 exerts an outward force on the base members 186a, 186b which creates a tension across the treatment area between the skin contact members 184.

The strength of the spring 187 and extent to which it is compressed are calibrated to establish a desired tensile force.

Each of the skin contact members 184 includes an array of barbs or microbarbs 194 projecting downwardly from a skin contacting surface 192. In contrast to the earlier embodiments, the skin contacting surfaces 192 are angled so as to better conform to a curvilinear surface, such as a patient's scalp (S, shown in phantom). More specifically, each of the skin contacting surfaces 192 forms an angle with a horizontal line drawn across the distal ends of the skin contact members 184, and which lies generally in a horizontal plane perpendicular to the vertical axis 188. The skin contacting surfaces 192 may be planar, or may also be slightly concave.

FIGS. 9A and 9B illustrate once again a skin tensioner 200 that has a closed-frame 202, which somewhat resembles a butterfly, and is termed "butterfly-style." FIG. 9A shows the frame 202 having been compressed or collapsed inward, while FIG. 9B shows the frame in a relaxed configuration after removal of an external force. The frame 202 is flexible and lies generally in a plane and preferably comprises a single element, typically molded material and is configured such that it may be compressed inward from a relaxed position. In one embodiment, the frame may comprise a resilient material, elastic in nature. In another embodiment, flexibility may be attained by the structure, shape, gaps, thicknesses, and/or material selection, for example, incorporated into parts of or into the entire frame.

The flexible frame 202, in the example illustrated, includes four side sections 204 joined by four spring corners 206 that project diagonally outward therefrom. Any other even or odd number of the side sections and spring corners of the frame is within the scope of the invention, so the following description refers to the four side sections simply for illustration purposes only. The four side sections 204 are shown linear and arranged substantially in a square, although they may be arcuate and otherwise arranged in various geometrical patterns. In the illustrated embodiment, each of the four spring corners 206 has a thin beam 208 and a thick beam 209 extending outward from two adjacent side sections 204 and joined by an arcuate bridge 210. The spring corners essentially have a spring portion comprising of the more narrow and flexible beam 208 and the bridge 210, and a second (base) beam 209.

FIG. 9A shows the four side sections 204 displaced inward toward each other such that the gap between each pair of beams 208 tapers or narrows. The length of the beams 208 and material and shape of the arcuate bridges 210 render the frame 202 highly flexible in this manner. Conversely, in the relaxed configuration of FIG. 9B, the gap between each pair of beams 208 is substantially constant. It should be noted that the user compresses the frame 202 by squeezing together two of the side sections 204, as indicated by the inward arrows 211, which also causes the perpendicular side sections to converge toward the center by virtue of their inward concavity. It can be seen that the opening formed by the side sections 204 is smaller when the frame 202 is in its compressed state than in its relaxed state.

Each side section 204 features a plurality of perforations 212 for receiving barbs or microbarbs (not shown) as described above. Both FIGS. 9A and 9B are bottom views of the frame 202 illustrating skin contacting surfaces 214 on the bottom of each of the side sections 204. The barbs extend beyond the skin contacting surfaces 214 and provide an anchor for each of the side sections 204 on a skin surface. In some embodiments, the frame 202 may be made, for example, of a metal to be reusable, while the barbs and microbarbs may be made disposable, to be glued or otherwise temporary attached to the reusable frame. For example, a clip with a plurality of barbs, such as pins, may be removably attached to the frame, or to the skin contacting surfaces. Another variation is to use adhesive or Velcro to temporarily attach an array of barbs to the frame surfaces. Moreover, various fiducials visible under image guidance may be similarly attached to the frame, thus providing a convenient reference framework for aiming follicular unit removal or implant tools.

In a skin tensioning procedure, a user compresses the frame 202 into the configuration shown in FIG. 9A by squeezing the two opposed side sections 204 in the direction of arrows 211 (as mentioned, the other two sides also bow inwardly). Accordingly, a method of applying tension to a body surface may comprise compressing a frame of a tensioning device in N directions (for example, N=2) to cause the frame to compress in more than N directions. More specifically, the method may comprise compressing a frame of a tensioning device to a compressed configuration, the tensioning device having at least three contact members, each contact member having at least one skin grasper; and releasing the frame to a relaxed configuration; wherein compressing the frame comprises compressing two of the at least three contract members to cause the at least three contact members to converge; and wherein releasing the frame to the relaxed configuration comprises facilitating tensioning of the body surface when the at least one skin grasper is engaged in the body surface.

As the opposing side sections 204 are arranged to be substantially square, eventually the four side sections 204 will be prevented from moving further when the corners of the side sections 204 meet each other. However, if the opposing side sections 204 are arranged to form a rectangular configuration, with the opposing side sections 204 that are squeezed in the direction of arrows 211 being shorter than the other opposing sides 204, improved tensioning may result. Altering the dimensions of the opposing sides in this manner may enable, for example, the end perforations 216 and 217 on the opposing side sections 204 to move inwards until they reach the point at which the perforations 215, 216, 217 and 218 form a substantially straight line. In this manner, the perforations may be configured to form a rectangular arrangement of equidistant perforations, even at the corners, thus facilitating a more uniform tension to be attained. The four side sections 204 can then be pressed onto a skin surface surrounding an area of treatment such that the barbs (or similar skin grasper expedient) engage the skin surface. After releasing the frame 202, the four side sections 204 are biased outward by the resiliency of the spring corners 204, thus placing the skin surface in tension. Because of the configuration of the illustrated frame 202, the tension is primarily bi-axial, although other shapes of frame such as annular, hexagonal, triangular, etc. could be utilized for a more omni-directional tension. The device of this invention may be made out of various materials, including metal or plastic. It could be also made disposable.

Figure 10A:
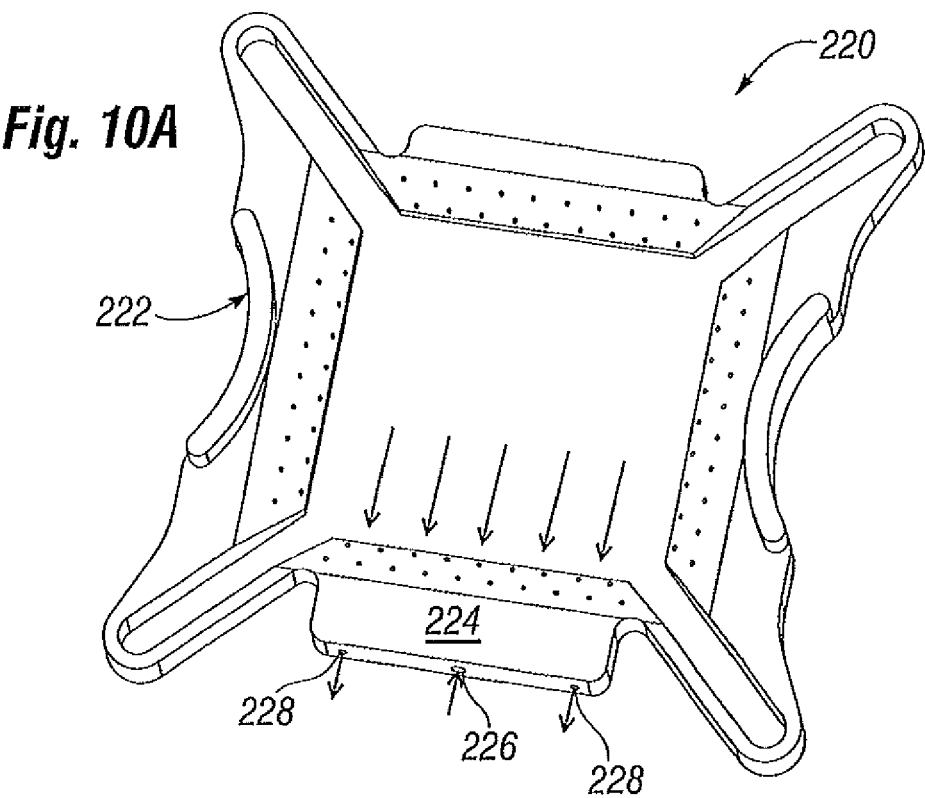
FIGS. 10A and 10B are top and bottom perspective views, respectively, of an alternative butterfly-style skin tensioner frame that incorporates a fluid flush to remove blood from the operating field.
Figure 10B:
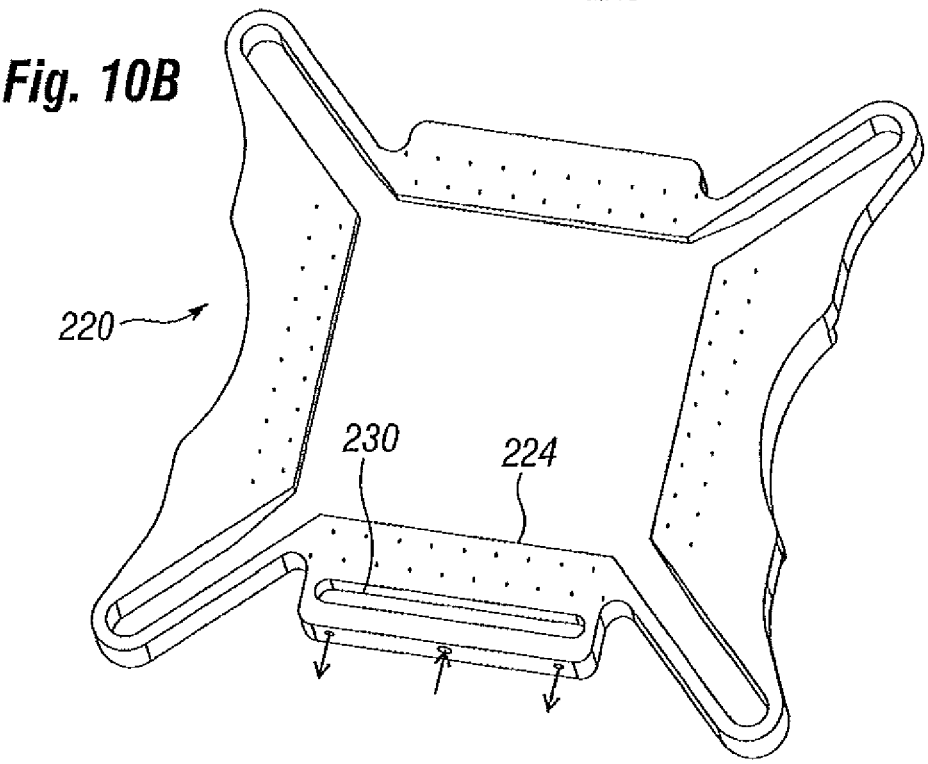

FIGS. 10A and 10B are top and bottom perspective views, respectively, of an alternative butterfly-style skin tensioner 220 that incorporates a fluid flush to remove blood from the operating field. The elements of the frame 222 of the tensioner 220 are similar to those described above with respect to FIGS. 9A and 9B, and will not be repeated. Of course, the reader will understand that the fluid flush could be incorporated in any of the skin tensioner designs described herein.

At least one of the side sections 224 of the frame 222 includes fluid flow channels therein. Saline or other inert fluid may be supplying through a port 226 in the side section and distributed to the treatment area within the frame 222 through the side section 224, or from around the periphery of the treatment area through all of the side sections. The fluid irrigation will mix with any blood or other fluids in the treatment area, and aspirating ports 228 in the side section 224 provide suction to remove excess fluid. In this regard, a lateral recess 230 in the underside of the side section 224 provides a reservoir which distributes the suction along one side of the treatment area such that a gradient is created to aspirate excess fluid more effectively. One particularly advantageous feature of the embodiments shown in FIGS. 9A, 9B, 10A and 10B is that it allows a single-hand operation of the device by pushing, for example, two sides 222 with a thumb and a finger, which results in all four sides moving accordingly.

Figure 11A:
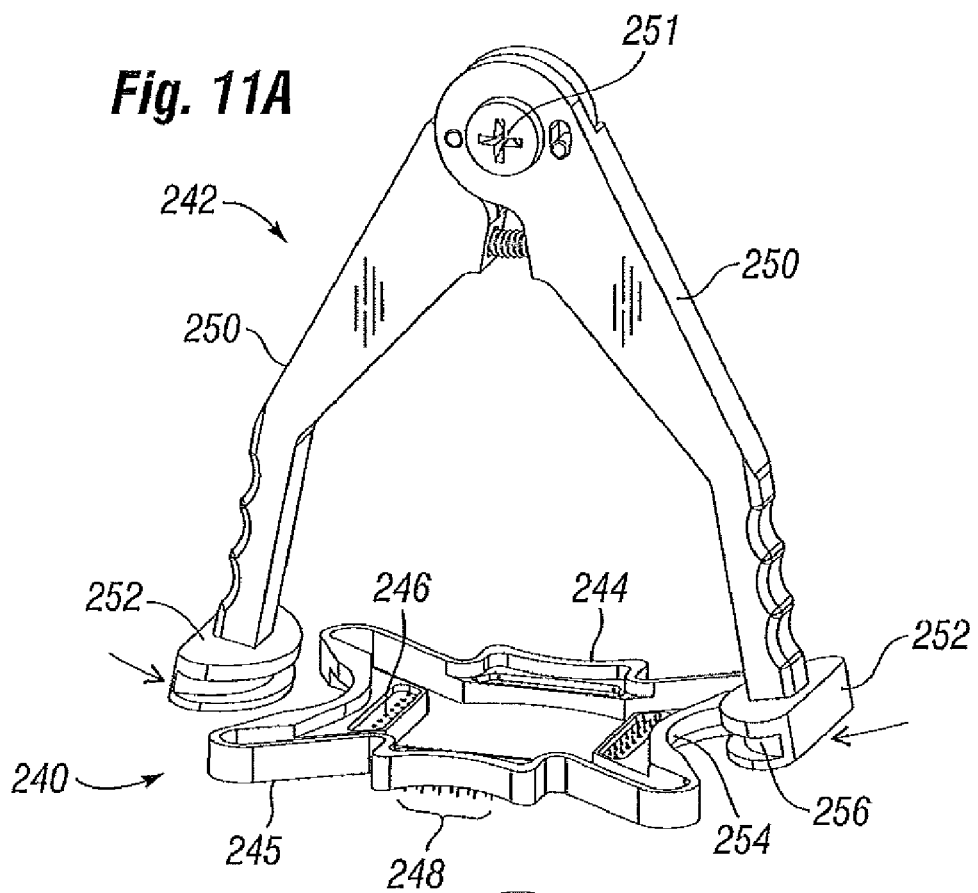
FIGS. 11A and 11B are perspective views of yet another alternative butterfly-style skin tensioner together with a compression tool.
Figure 11B:
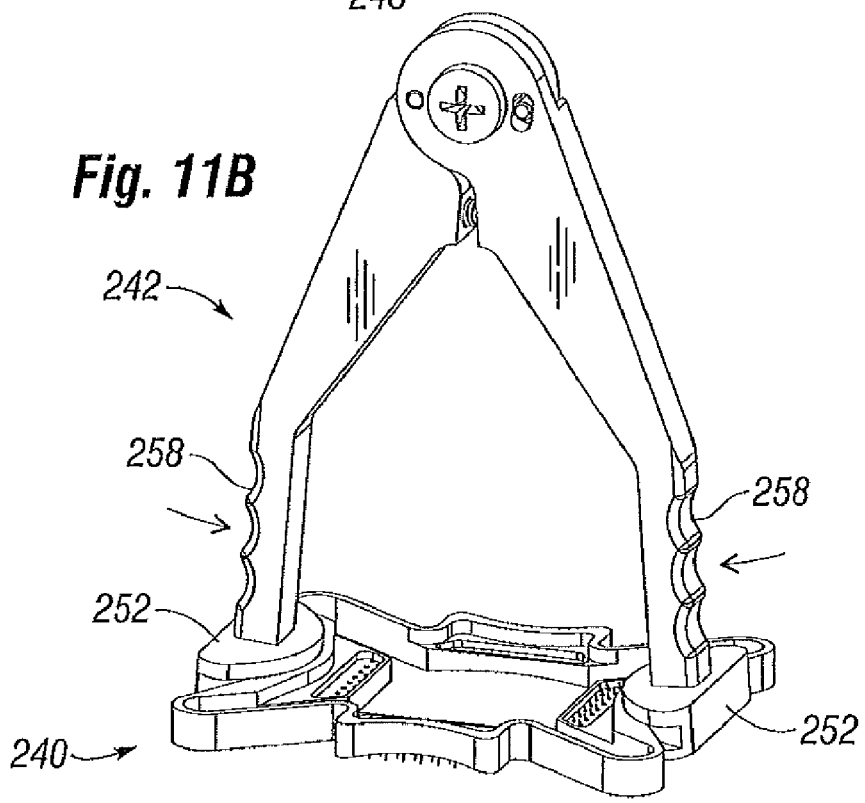

FIGS. 11A and 11B illustrate an alternative butterfly-style skin tensioner 240 together with an aid or tool 242 that facilitates deployment thereof. As before, the skin tensioner 240 may lie generally in a plane and includes a frame, for example, with four side sections 244 joined by four spring corners 245 that project diagonally outward therefrom. Each side section 244 features skin contacting surfaces 246 on which are positioned skin graspers, e.g., a plurality of barbs or microbarbs 248, as described above. The reader will notice a slight concavity to the underside of the frame of the skin tensioner 240 which helps conform or wrap the skin contacting surfaces around convex skin surfaces.

In the case of a relatively small sized butterfly frame, the user may experience difficulty compressing it while simultaneously positioning the frame over a treatment area and pressing down to engage the barbs. Consequently, a compression tool 242 may be utilized to simplify the procedure. One example of a compression tool 242 illustrated in FIGS. 11A and 11B comprises a compass-like clamp with two bifurcated legs 250 connected at a hinge 251. The distance between the two bifurcated legs 250 can be reduced to accommodate smaller hands, or sized appropriately for the user. The free ends of the legs 250 terminate in blocks 252 each of which in this example is shaped to conform to an outer edge of one of the side sections 244; while conformance is beneficial for better fitting, it is not necessary. In the illustrated embodiment, the blocks 252 each have a convex groove 256 that receives a concave lip 254 on opposite side sections 244. In use of this particular configuration, the user may hold the compression tool 242 such that the general plane of the tool is substantially orthogonal to the frame of the body surface tensioning device 240, in a "top-mounted" fashion. The user engages the blocks 252 with the opposed side sections 244, so that the tool grasps the tensioning device over the outer edges thereof, and with one hand squeezes inward on finger grips 258, thus compressing the frame. The finger grips 258 and the area over which the finger grips extend can be sized and shaped to accommodate various hand sizes, and to reduce the force exerted on the user's hands during operation. When utilizing the tool in this manner, sometimes the user may find that removal of the compression tool from the frame is hindered by the frame of the tensioner having conformed to the shape of the body surface.

Figure 11C:
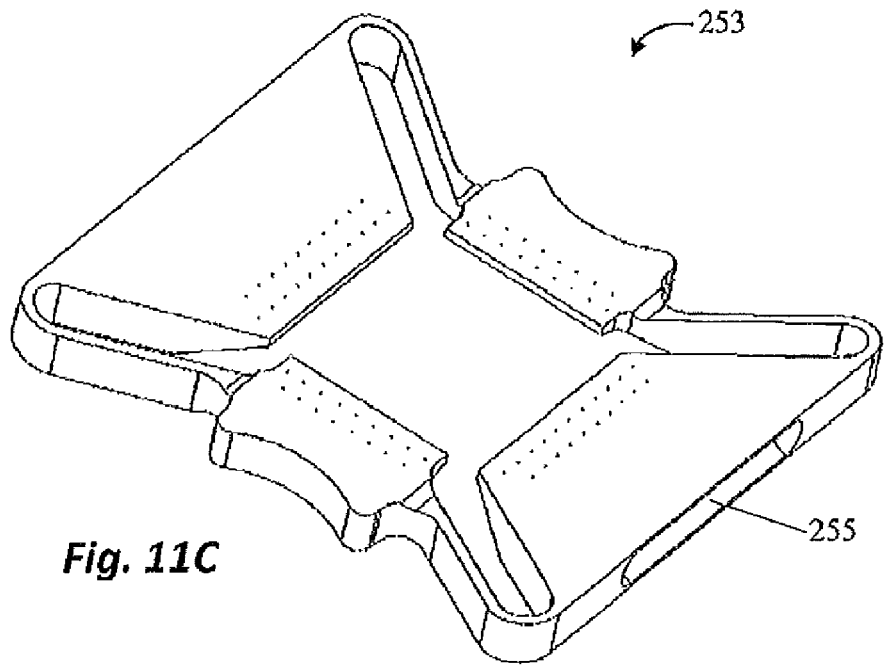
FIG. 11C is a perspective view of a further alternative skin tensioner.

In an alternative configuration of the tensioner illustrated in FIG. 11C, recesses in the substantially planar frame may enable the user to more easily remove the compression tool from the tensioning device. FIG. 11C illustrates a skin tensioner 253 which has recesses 255 formed in the outer edges of the skin tensioner 253. These recesses 255 provide a specified location where a suitably adapted compression tool can grasp and compress the tensioning device 253. The recesses 255 provide a location from which the tool can be more easily maneuvered to aid in its removal from the frame of the tensioning device, whether or not it has changed shape to conform to that of the body surface. The recess feature may enable the user to more easily compress and relax the skin tensioner with only one hand.

Figure 11D:
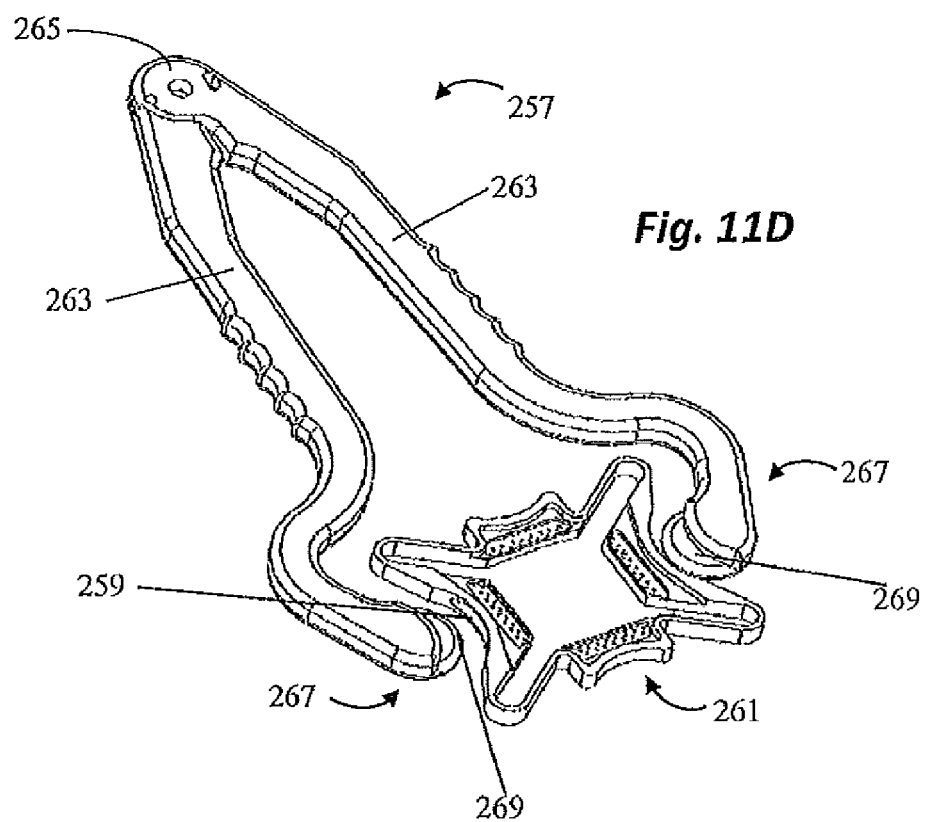
FIG. 11D is a perspective view of the alternative skin tensioner of 11C together with an alternative compression tool.

The tool illustrated in FIG. 11D is adapted to not only grasp a skin tensioning device 257 via recesses 259 disposed on the outer edges of the skin tensioning device 261, but is also adapted to be used with the general plane of the compression tool 257 substantially parallel to the frame of the body surface tensioning device 261. The use of this "side-mounted" compression tool 257, in combination with a recessed tensioning device 261, may reduce twisting that the tensioning device 261 may experience when the user is compressing the frame.

The compression tool illustrated in FIG. 11D comprises a compass-like clamp with two bifurcated legs 263 connected at a hinge 265. Similarly to the previously described tool, the distance between the bifurcated legs, the sizing of the finger grips and the area over which the finger grips extends, can be configured to optimize performance of the device based on the intended user. The free ends of the legs 263 terminate at the distal end in end portions 267 which may be shaped to correspond to an outer edge of one of the side sections 244. In the illustrated embodiment, the end portions comprise a protruding section that is configured to correspond to a recess or a notch located in the opposite side sections 244, and a side section that is configured to be positioned adjacent the opposite side sections 244. In use of this particular configuration, the user holds the compression tool 257 such that the general plane of the tool 257 is substantially in plane with the frame of the body surface or skin tensioning device 261. The user engages the protruding sections 269, for example, into recesses or notches on the opposed side sections 244 and with one hand squeezes inward on finger grips, thus compressing the frame. When the body surface tensioning device 267 has been placed on the body surface, and the skin graspers, e.g. barbs, have engaged the body surface, the user releases his grip on the compression tool 257, the frame of the tensioning device 261 returns to its relaxed configuration, and the protruding sections 269 are removed from the recesses of the frame.

As suggested earlier, the manner in which the compression tool is utilized may also facilitate a reduction in twisting of the frame of the tensioning device. Since the bifurcated legs of both compression tools illustrated are connected with a hinge, it will be apparent that the ends of the legs move radially about the hinge. When utilized in the fashion of a top-mounted compression tool, in use the radial movement may be conveyed to the frame and cause planar distortion, for example in the form of twisting of the frame as it is compressed and/or released. By utilizing the compression tool in a side-mounted manner, the radial motion of the ends of the legs has less influence on the frame of the tensioning device, particularly if recesses are formed in the frame. An added advantage is the improved visual access of the treatment area for the user.

Figure 12A:
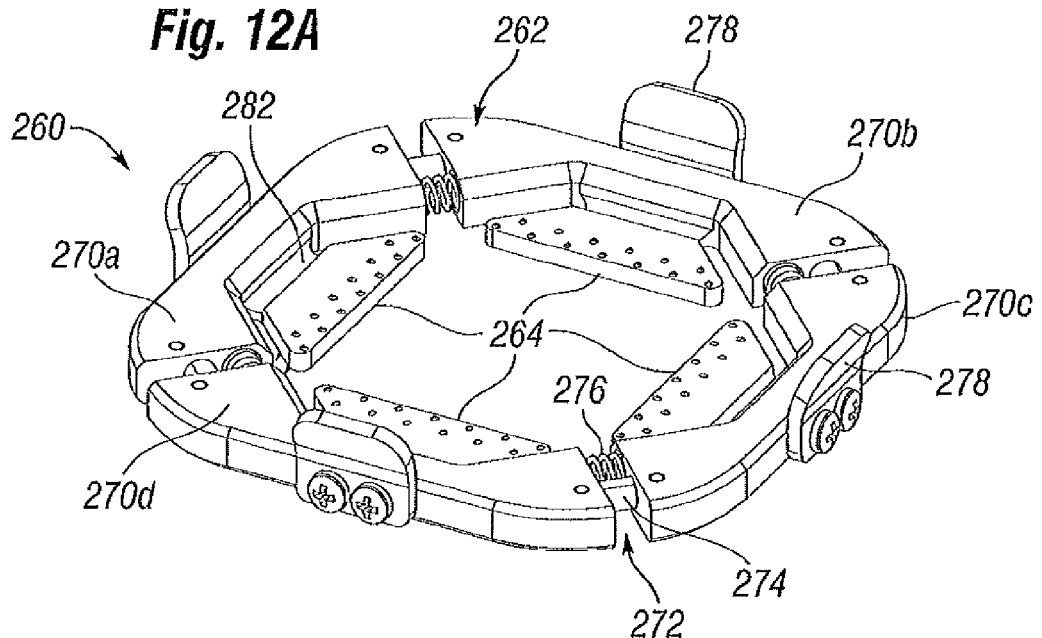
FIGS. 12A and 12B are top and bottom perspective views, respectively, of a still further alternative skin tensioner having a closed-loop frame and four contact members each incorporating skin graspers.
Figure 12B:
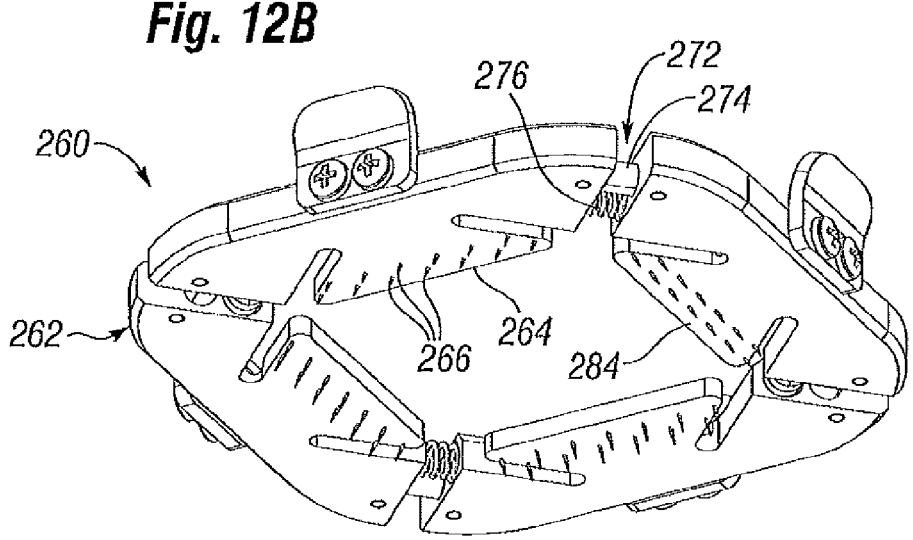

FIGS. 12A and 12B are top and bottom perspective views, respectively, of a still further alternative skin tensioner 260 having a closed-loop frame 262 and four contact members 264 each incorporating barbs 266. The frame 262 has a substantially square configuration, with four identical quadrants. Of course, as explained above, the principles embodied in this version may be translated to other shapes, and even to frames that are open as opposed to a closed shape.

The frame 262 comprises four side segments 270a-d that are coupled to each other across corner gaps 272. Adjacent side segments 270 translate toward and away from one another via shafts 274, and are biased away from each other by springs 276. Much like the butterfly-style of frame described above, the four side segments 270a-d may be compressed inward toward each other along the shafts 274 against the bias of the springs 276. Thumb tabs 278 project upward from and help in manipulating the side segments 270a-d.

Each side segment 270a-d includes an inwardly-directed contact member 264 connected thereto via a flexible junction 282 (e.g., a living hinge). The flexible junction 282 allows for some rotation and movement of the contact member or pad 264 out of the plane of the side segments 270 to accommodate a skin surface curvature, for example, when working on patient's head. The contact members 264 are able to flex in a vertical direction relative to and generally perpendicular to the plane defined by the side segments 270a-d. An array of barbs 266 projects downward from a skin contacting surface 284 on the bottom of each pad 264. In the illustrated embodiment, each contact member 264 comprises a rounded trapezoidal pad that broadens toward the center of the frame 262. As seen in FIG. 11B, the barbs 266 angle outward way from the center of the frame 262 for greater purchase on the skin when pulled outward.

In use, the technician or any user compresses the frame 262 such that the side segments 270a-d move toward each other against the springs 276 so as to narrow the gaps 272. The user then presses the skin tensioner 260 against the patient such that the frame 262 surrounds the treatment site and the barbs 266 engage the skin surface. The flexible nature of the contact members 264 helps to conform the aggregation of pads to a rounded surface, such as a scalp. Upon release of the frame 262 the side segments 270a-d tend to move away from one another, thus causing the contact members 264 and barbs 266 to apply tension in four outward directions to the skin surface in the treatment area.

Figure 13:
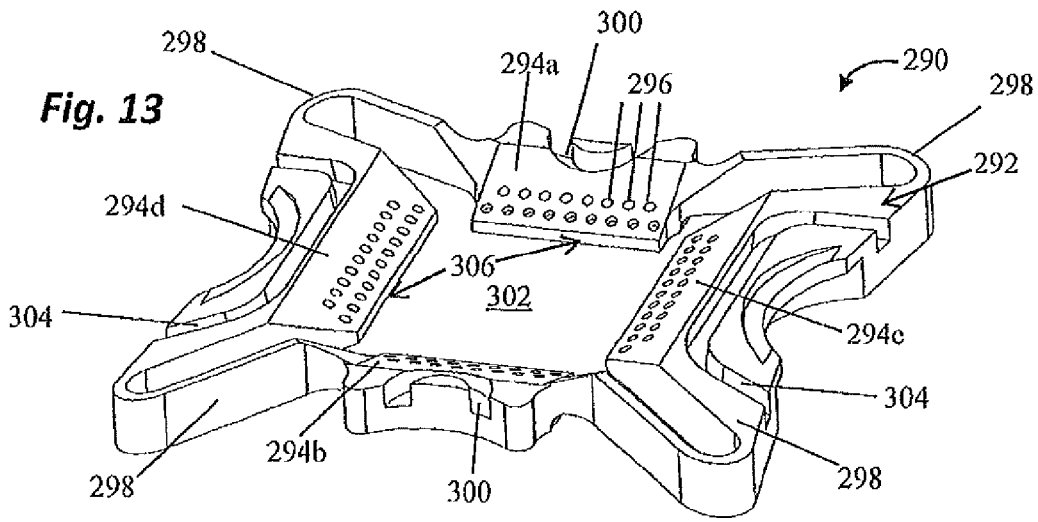
FIG. 13 is a top perspective view of yet a further alternative body surface tensioner, in a relaxed configuration.

FIG. 13 illustrates yet another embodiment of a "butterfly-style" body surface tensioning device or tensioner 290 shown as a top perspective view, in a relaxed configuration. The frame 292 is flexible and is configured such that it may be compressed inward from a relaxed position. The frame 292 comprises, as an example, four contact members 294a-d, the top surfaces of which are illustrated in FIG. 13. Any or each contact member 294a-d may feature a plurality of optional perforations 296 for receiving skin graspers, such as barbs or microbarbs (not shown) as described above. The perforations although illustrated as extending from the top to the bottom surface of the contact members 294a-d, may take other forms, such as recesses in the underside or a bottom surface of the contact members that do not extend all the way to the top surface of the contact members. Alternatively, no perforations 296 may be present, and the skin graspers may be, for example, located or formed on, or otherwise connected to the underside (or bottom) surface 306 of the contact members. The barbs extend beyond (below) the underside or the bottom surface 306 of the contact members and provide an anchor on a body surface. This particular configuration shows the top surfaces of the contact members 294a-d being angled or inclined with respect to the body surface on which the contact members will make contact. The inclined top surface is illustrated as one continuous surface tapered down towards a center of an opening 302, however alternative configurations and other geometries to accomplish the incline, such as one or more steps or chamfers, for example, may be used. This angled top surface may be useful when the tensioner is to be used in conjunction with a treatment tool (for example, hair harvesting tool), enabling the tool to be more easily angled with respect to the treatment area defined by the opening 302 formed by the inwardly-facing edges of the contact member 294a-d. The angled top surfaces may be particularly useful when the tensioning device 290 is to be used in conjunction with a robotic, or an automated tool. In addition, when utilizing an automated or robotic system, the angled configuration of the top surface of the contact members also provides a more open or wide-angled view to be observed by any imaging device that may be utilized.

Although the contact members 294a-d in this embodiment lie in a general plane, the four flexible corners 298 that join the four side sections may be angled (e.g. down) with respect to this general plane. The curvature of the frame created by the angled flexible corners 298 is such that when in use, the frame 292 rests closer to the body surface in question. The curvature may be symmetrical or asymmetrical across the frame 292, and may be appropriately shaped to fit the body surface in question.

The frame 292 may also comprise one or more channels or grooves 300 for receiving a strand (not shown) therein. The strand may be relatively flexible, inflexible, relatively elastic, or inelastic, depending upon the purpose(s) for which it is to be used. Similarly to the strand 32 discussed in reference to FIG. 2, possible uses of the strand may include for example, the maintenance of the engagement of the contact members 294a or 294b to the body surface, and/or the creation of additional tension across the body surface. In the situation of the tensioning device 290 is being used to harvest hair from a donor area on the skin, the strands may be used to alter the angle of the hair follicles that protrude from the body surface within the opening 302 formed by the edges of the contact member 294a-d when the frame 292 is placed on the body surface. The frame may also have one or more additional grooves 304 for receiving strands (also not shown) in one or more of the contact members. These can be used, for example, to secure the frame 292 in place during treatment.

As illustrated in FIG. 13, the bottom surfaces of the contact members which are configured to contact the body surface, for example surfaces 306, are substantially flat. However, as illustrated in yet another embodiment of the tensioner 310 of FIGS. 14A and 14B, a bottom surface 306 of any one or more of the contact members 312a-d may be curved or formed such that when in use, the frame conforms better to the body surface in question. The curvature may be symmetrical or asymmetrical across the bottom surfaces of the contact members 312a-d, and may be appropriately shaped to fit the body surface in question. In one particular configuration, for example when used to assist in hair harvesting from a donor area on the scalp, one or more of the bottom surfaces of the contact members 312a-d may comprise a spherical radius to approximate to the shape of the scalp. However the center of the spherical radius of bottom surface of one contact member does not necessarily have to match the center of the spherical radius of the bottom surface of another adjacent contact member. For example, in the illustrated embodiment of FIGS. 14A and 14B, the bottom surfaces of the two sets of opposing contact members may have their respective spherical radius offset such that one set of opposing contact members contacts the body surface, in this case the scalp, before the other set of opposing contact members.

In the example of a tensioning device being used to assist the user in harvesting hair from a donor area, the user compresses the frame by squeezing together the two sides of the tensioning device 290, with a tool as described hereinbefore. Having done so, the user then pushes the contact members 294a-d onto a body surface such that the barbs/skin graspers engage the body surface. However, the user may find that while he/she is able to provide sufficient force to keep the barbs engaged in the body surface via the contact members associated with the compression tool (e.g. 294c and 294d in FIG. 13), the other contact members 294a and 294b that are not held by the compression tool may lift from or otherwise will not firmly contact the body surface. The user may have to use one hand to push the contact members 294a and 294b towards the body surface, and the other hand to hold and operate the tensioning device 290.

Figure 14A:
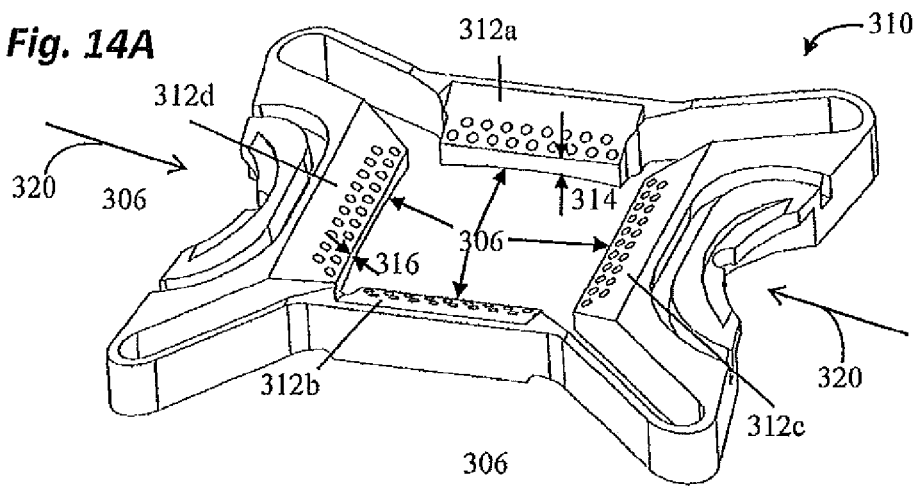
FIGS. 14A and 14B are top and bottom perspective views, respectively, of an alternative butterfly-style skin tensioner frame that incorporates grooves to additionally secure and tension the device.
Figure 14B:
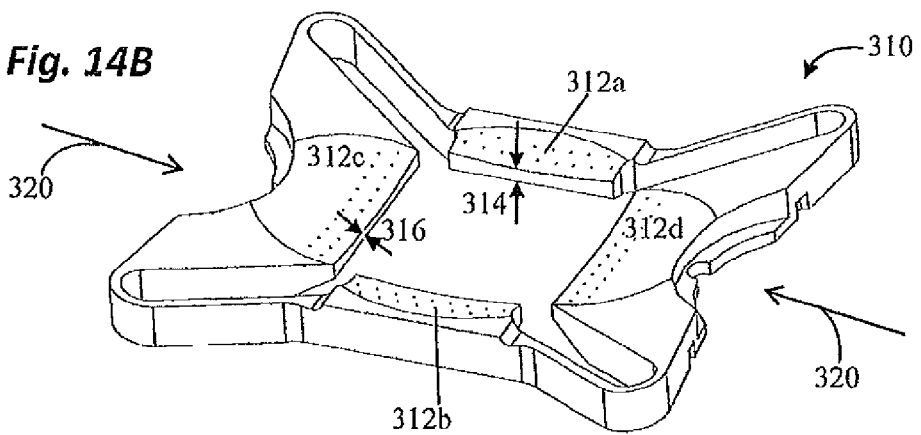

FIG. 14B is a bottom view of the tensioner 310 of FIG. 14A illustrating the bottom surfaces of the contact members 312a-d. Unlike the previous embodiment illustrated in FIG. 13, the visible bottom surfaces of the contact members 312a and 312b are positioned in a different general plane (as explained above, it could be a curved general plane) from the visible bottom surfaces of the contact members 312c and 312d. In other words, if these bottom surfaces were placed on the treatment area of the body, one of the opposing sets of these bottom surfaces (e.g. of the contact members 312a and 312b) would contact the treatment area first before the other set. There are various ways in which this configuration can be achieved, one of which is described herein. FIGS. 14A and 14B illustrate a configuration in which the top surface of all the contact members 312a-d are in a first general plane. The bottom surfaces of the contact members 312a and 312b lie in a second general plane, and the bottom surfaces of the contact members 312c and 312d lie in a third general plane. In use, this particular configuration aids the user in more easily operating the tensioner with only one hand. Utilizing the embodiment illustrated in FIGS. 14A and 14B, the user would find that the contact members 312a and 312b would engage the body surface prior to the contact members 312c and 312d. In this particular embodiment, the above-described configuration is achieved by forming two of the contact members 312a and 312b to be of differing heights with respect to the other two contact members 312c and 312d. As illustrated in the embodiment shown, the depth 314 of the contact members 312a and 312b is greater than the depth of the contact members 312c and 312d, referenced from the first plane in which the top surface of all the contact members 312a-d lies. In the example of a tensioning device being used to assist the user in harvesting hair from a donor area, the user would compress the frame by squeezing together the two sides of the tensioning device 310 in the direction, as indicated by the inward arrows 320, with a tool as described hereinbefore. With the embodiment illustrated in FIGS. 14A and 14B, the user would find that the contact members 312a and 312b would engage the body surface prior to the other contact members 312c and 312d. By so doing, the barbs received therein would take hold of the body surface, and be less encouraged to lift from the body surface as the user continued to push the remaining two contact members 312c and 312d to engage in the body surface. As indicated earlier, it will be apparent that the difference in the disposition of the bottom planes (including the curved planes) associated with the respective contact members may be facilitated in other manners, not described herein, but which are within the scope of the inventions described herein.

Figure 15A:
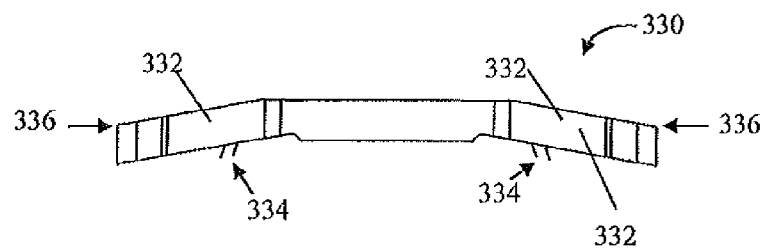
FIGS. 15A and 15B illustrate the angle of the barbs with respect to the body surface being substantially the same when the frame is both compressed and relaxed.
Figure 15B:
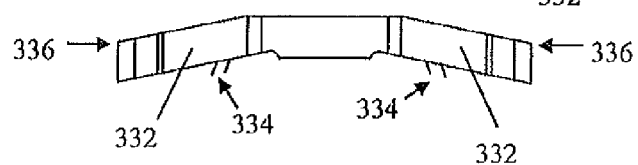

In order for a butterfly frame-type device to adequately maintain engagement during the tensioning process, and during the length of a treatment procedure, the barbs described are typically angled to be other than orthogonal with respect to the body surface. At this orientation, the barbs encounter resistance from the body surface and are more easily retained therein. FIG. 15A shows a side view of a frame of a generally planar tensioning device 330. FIG. 15A show the device 330 in the relaxed or uncompressed configuration, and FIG. 15B shows the device 330 in a compressed configuration. The frame comprises contact members 332 that are curved in the particular illustration, having skin graspers 334 that extend therefrom. In use, in order to move the frame configuration from the relaxed configuration of 15A to the compressed configuration of FIG. 15B, the user must apply a compression force to the frame. If the user were to use a tool similar to that illustrated in FIG. 11A or 11B, the compressional force would generally be applied at the points 336 indicated in FIG. 15B, by gripping the tensioning device from above. Application of a compressional force causes the frame to be compressed substantially in the plane of the frame, and in such a way that the barbs would remain at substantially the same angle as in the relaxed or uncompressed configuration. As illustrated, the points 336 at which the compressional force is applied are relatively high up on the frame itself. Consequently, when compressed in this manner, the compression is generally in the same plane as the frame of the tensioner itself. The movement of the barbs therefore, is generally translational and not rotational. That is, the orientation of the barbs with the respect to the body surface is substantially maintained. The desired angle of the barbs with respect to the body surface is optimized to provide adequate retention within the body surface, typically over a period of time required to complete a procedure or a step in the procedure. However, the same angle of the barbs designed to provide adequate retention may contribute to the difficulty experienced by the user in initially engaging the barbs into the body surface. As a consequence, and due to the relatively small size of the butterfly frames, the user may also experience difficulty in pressing down and engaging the barbs in the patient's body surface, while simultaneously compressing and positioning the frame over a treatment area.

Figure 16A:
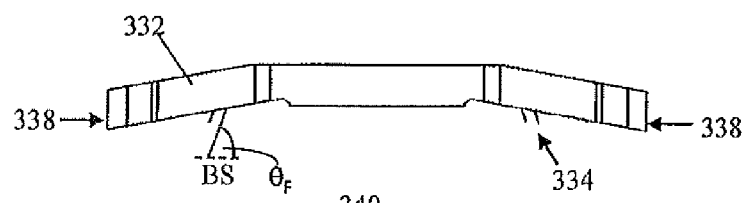
FIGS. 16A and 16B illustrate the angle of the barbs with respect to the body surface being at a first angle when the frame is compressed, and at an angle other than the first angle when the frame is relaxed.
Figure 16B:
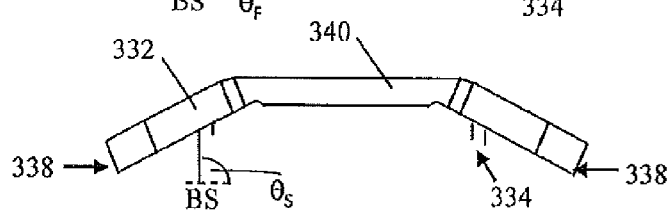

FIGS. 16A and 16B illustrate an alternative embodiment providing an improved engagement of the tensioner with the body surface. FIG. 16A is similar to that of 15A. The skin graspers, e.g. barbs 334 are shown as being at a first angle $\theta_F$ with respect to the body surface BS, just as in FIG. 15A, however the figure shows the compressional force being applied at a lower point 338 with respect to the plane of the frame of the tensioning device 330. Such a compressional force may be applied using a compression tool such as the one illustrated in FIGS. 11C and 11D. A tool of this nature not only facilitates gripping of the tensioner 330 from the side, but at a lower point. The compression tool such as the one illustrated in FIGS. 11A and 11B (the tool that is used in the upright position) may also be utilized, provided that it is adapted to apply compressional forces at the desired location. When compressed in this manner, in the configuration illustrated, the sections 340 of the frame are raised, and the skin contact members 332 are forced in a downward direction as illustrated. The movement of the respective members 332 and 340 causes the orientation of the barbs 334 with respect to the tensioner to change, to an angle $\theta_S$ other than the first angle $\theta_F$ and in this instance becomes more orthogonal to the body surface BS. The change in orientation of the barbs 334 assists the user in engaging the barbs with the body surface. In the orientation substantially orthogonal to the body surface, the barbs encounter less resistance from the body surface and penetrate it more easily. Once engaged, the user relaxes his grip and the compressional forces are released. The movement of the respective contact members or sections 332 and 340 causes the orientation of the barbs 334 with respect to the body surface tensioning device to change once again, back to the first angle $\theta_F$, becoming less orthogonal to the body surface BS, and encountering more resistance, such that the barbs are retained in the body surface. According to the above described embodiment, a method of applying tension to a body surface may comprise moving a frame of a tensioning device from a compressed configuration to a relaxed configuration such that to cause at least one skin grasper, such as a barb, positioned on the frame to move from a first angle relative to the body surface to a second angle relative to the body surface. In certain embodiments, the method comprises compressing a frame of the tensioning device (the frame includes a skin contact member with a plurality of skin graspers) to a compressed configuration such that at least one of the plurality of the skin graspers is disposed at a first angle with respect to the body surface; and releasing the frame to cause the least one of the plurality of the skin graspers to move from the first angle with respect to the body surface to a second angle other than the first angle, thereby creating tension across the body surface in a treatment area between the plurality of the skin graspers. The method may further comprise removing a hair graft from the area of the body surface under tension or implanting a hair graft into the area of the body surface under tension.

Figure 17:
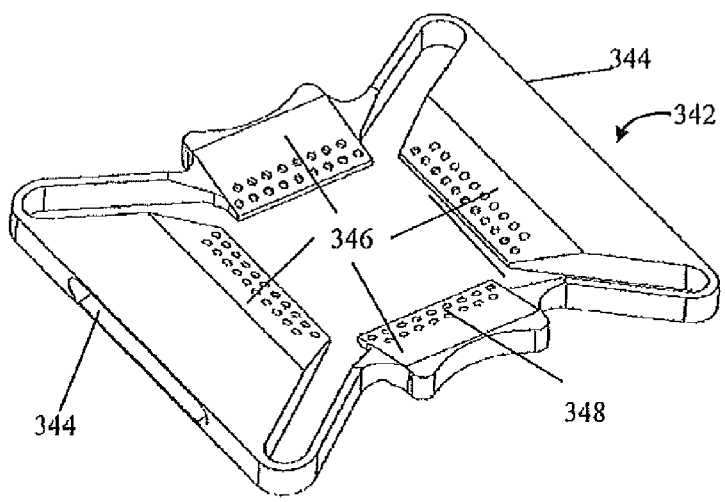
FIG. 17 is a perspective view of yet another alternative body surface tensioning device.

FIG. 17 illustrates yet another alternative tensioning device 342 and corresponding method of applying tension which exhibits the properties described in relation to FIGS. 16A and 16B. The example illustrated shows a flexible frame 342 comprising four contact members 346, each of the contact members 346 featuring a plurality of optional perforations 348 for receiving barbs or microbarbs (not shown) as described above. In the relaxed configuration corresponding to that illustrated in FIG. 15A, the top surface of the contact member 346 is angled in a downward fashion towards the center of the frame 342 with respect to the body surface. The perforations 348, if present, are also angled, or if no perforations are present, the skin graspers are angled.

In a skin tensioning procedure, a user compresses the frame 342 into the configuration shown in FIG. 17 by squeezing the two opposed side sections that have recesses 344. As mentioned in previous embodiments, the other two sides also bow inwardly. As the sides move inwards, the more central portion of the skin contact members (or contact members) 346 are caused to lift, and the more outwardly disposed portions of the contact member 346 remain substantially at the same level, due to the flexibility of the frame. As the result of the above compression, the initially angled skin graspers are caused to be reoriented to be substantially orthogonal to the body surface, and therefore can more easily be engaged in the body surface. The contact members 346 are then pressed onto the body surface surrounding an area of treatment such that the reoriented barbs (or similar skin grasper expedient) engage the skin or body surface. After releasing the frame 342, the contact members 346 return to their relaxed configuration and the barbs assume its original angled configuration, which in turn provides for improved retention of the tensioner with the body surface.

It will be apparent that the change in orientation may be facilitated by means other than those described above in reference to the examples of FIGS. 15-17. For example, the compression tool can be configured a certain way to apply the compressional forces to the tensioning device to enable the change in the barbs orientation to occur, or the shape of the tensioning device may be configured to ensure the compressional forces are applied in a desirable location, or the materials may be selected so that the frame compresses in a desirable manner, or the overall design of the tensioning device and/or compression tool may be such that all involved elements facilitate the end result, and/or any other means may be considered to facilitate the change in orientation of the barbs.

It is to be understood that the words which have been used are words of description and not of limitation, and those skilled in the art will recognize that various modifications and improvements may be made to the inventions described herein without departing from the scope thereof, Moreover, although individual features of one embodiment may be discussed herein or shown in the drawings of the one embodiment and not in other embodiments, it should be apparent that individual features of one embodiment may be combined with one or more features of another embodiment or features from a plurality of embodiments. Therefore, changes may be made within the appended claims without departing from the true scope of the present application.

What is claimed is:

1. A device for applying tension to a body surface, comprising:
    a flexible frame comprising a central opening, at least three skin contact members, and at least one skin grasper;
    the flexible frame configured to move between a compressed configuration and a relaxed configuration such that compression of two of the at least three skin contact members towards the central opening causes the at least three skin contact members to converge towards and reduce the size of the central opening, the flexible frame is biased in the relaxed configuration, wherein in the relaxed configuration, when the at least one skin grasper is engaged in the body surface, the flexible frame is configured to provide tension in the body surface; and
    wherein the frame comprises one or more fiducials visible under image guidance.

2. The device of claim 1, wherein at least a portion of the flexible frame comprises a resilient material.

3. The device of claim 1, wherein the flexible frame comprises portions that are shaped and/or of a thickness to render the flexible frame flexible.

4. The device of claim 1, wherein the at least three skin contact members are connected by flexible corners.

5. The device of claim 1, wherein the flexible frame comprises a closed-loop configuration defining the opening.

6. The device of claim 1, wherein when positioned on the body surface in the relaxed configuration, the flexible frame provides substantially uniform tension across the body surface.

7. The device of claim 1, wherein the flexible frame is configured to conform to the body surface.

8. The device of claim 1, wherein the skin grasper comprises one or more of a barb, a microbarb, an adhesive, or a rough surface texture.

9. The device of claim 1, wherein the skin grasper comprises at least a first barb and a second barb, the first barb being angled away from the second barb.

10. The device of claim 1, wherein the skin grasper is a barb or a microbarb, and when positioned on the body surface, in the compressed configuration the barb is directed at a first angle relative to the body surface, and in the relaxed configuration the barb is directed at a second angle relative to the body surface.

11. The device of claim 1, wherein the at least one skin grasper is located on a skin contacting surface of one of the at least three skin contact members and the one or more fiducials is located on a surface opposite to the skin contacting surface.

12. The device of claim 1, wherein the frame is molded.

13. The device of claim 1, wherein a first of the at least three skin contact members lies in a first plane, and a second of the at least three skin contact members lies in a plane other than the first plane.

14. The device of claim 4, wherein the frame has a butterfly-style shape with two generally parallel side sections perpendicular to two other generally parallel side sections, and the flexible corners extend generally diagonally outward from a center of an opening defined by the side sections.

15. The device of claim 1, wherein the flexible frame is generally planar in the relaxed configuration, and the frame is configured such that a portion of the frame flexes out of the plane when the flexible frame is compressed.

16. The device of claim 1, further comprising an input port for delivering a fluid to the body surface, and an output port for removing fluid from the body surface.

17. The device of claim 1, wherein one of the at least three skin contact members comprises a chamber such that, when positioned on the body surface, a vacuum can be created within the chamber to create suction between the contact member and the body surface.

18. The device of claim 1, wherein the device is configured and sized to tension the body surface containing hair follicles to facilitate harvesting of hair follicles from the tensioned body surface.

19. The device of claim 1, further comprising an digital indicator on the flexible frame that displays the magnitude of the tension being applied to the body surface.

20. The device of claim 1, further comprising a tension control on the flexible frame that enables adjustment of the magnitude of the tension being applied to the body surface.

21. A device for applying tension to a body surface, comprising:
    a flexible frame comprising two generally parallel skin contact sections perpendicular to two other generally parallel skin contact sections, the skin contact sections connected by flexible corners and each having a skin grasper;
    the flexible frame configured to move between a compressed configuration and a relaxed configuration and biased in the relaxed configuration to provide tension in the body surface;
    wherein one or more flexible corners comprise a beam projecting generally outward at an angle from adjacent skin contact sections that the flexible corner connects, the beam having a gap that separates the adjacent skin contact sections.

22. The device of claim 21, wherein when the flexible frame is in the compressed configuration, the gap is reduced relative to when the flexible frame is in the relaxed configuration.

23. The device of claim 21, wherein the beam comprises two elongated beam elements connected by a bridge.

24. The device of claim 21, wherein the flexible frame comprises a central opening and wherein compression of the two generally parallel skin contact sections towards the central opening causes the other two generally parallel skin contact sections to converge towards the central opening.

25. The device of claim 21, wherein when positioned on the body surface in the relaxed configuration, the flexible frame provides substantially uniform tension across the body surface.

26. The device of claim 21, wherein at least the skin contact sections of the flexible frame are configured to conform to the body surface.

27. The device of claim 21, wherein compression of two of the generally parallel skin contact sections causes the other two generally parallel skin contact sections to converge.

28. The device of claim 21, wherein the skin grasper comprises one or more of a barb, a microbarb, an adhesive, or a rough surface texture.

29. The device of claim 21, wherein the skin grasper comprises at least a first barb and a second barb, the first barb being angled away from the second barb.

30. The device of claim 21, wherein the flexible frame comprises one or more fiducials visible under image guidance.

31. The device of claim 21, wherein a skin contacting surface of the two generally parallel skin contact sections lie generally lower relative to a skin contacting surface of the other two generally parallel skin contact sections, such that when positioned on the body surface, the first two generally parallel skin contact sections contact the body surface before the second two generally parallel skin contact sections.

32. The device of claim 21, further comprising an input port for delivering a fluid to the body surface, and an output port for removing fluid from the body surface.

33. The device of claim 21, wherein each of the two generally parallel skin contact sections comprise a chamber such that, when positioned on the body surface, a vacuum can be created within the chamber to create suction between the skin contact section and the body surface.

34. The device of claim 21, wherein the device is configured and sized to tension the body surface containing hair follicles to facilitate harvesting of hair follicles from the tensioned body surface.

35. The device of claim 21, further comprising a tension control on the flexible frame that enables adjustment of the magnitude of the tension being applied to the body surface, the tension control comprising markings to provide a visual indication of the magnitude of tension force applied to the body surface.

36. The device of claim 21, wherein the flexible frame comprises a structure sized and shaped to provide engagement with a compression tool configured to compress the flexible frame.

37. A device for applying tension to a body surface, comprising:
 a flexible frame comprising a central opening and at least three skin contact members connected by flexible corners, each skin contact member having at least one skin grasper;
 the flexible frame configured to move between a compressed configuration and a relaxed configuration such that compression of two of the at least three skin contact members towards the central opening causes the at least three skin contact members to converge towards and reduce the size of the central opening;
 wherein the flexible frame is biased in the relaxed configuration to provide tension in the body surface within the central opening of the flexible frame.

38. A compression tool for use with the device of claim 37, wherein the compression tool is shaped to engage the flexible frame and is configured to cause the flexible frame to move between the compressed and the relaxed configuration.

39. The tool of claim 38, wherein the flexible frame lies generally in a first plane, and the compression tool is configured to be positioned generally in a second plane when causing the flexible frame to move between the compressed and the relaxed configuration.

40. The compression tool of claim 39, wherein the second plane is substantially parallel or substantially orthogonal to the general plane of the flexible frame.

41. The device of claim 27, wherein the flexible corners are shaped and/or of a thickness to render the flexible frame flexible.

42. The device of claim 37, wherein the at least three skin contact members comprises four contact members, and compression of two of the four skin contact members towards a central opening causes the four skin contact members to converge towards the central opening.

* * * * *